United States Patent [19]

Lumma, Jr. et al.

[11] Patent Number: 5,051,422
[45] Date of Patent: Sep. 24, 1991

[54] 2-SUBSTITUTED-1(4)-ARYL PIPERAZINES AND THE PROCESS FOR THEIR PREPARATION

[75] Inventors: William C. Lumma, Jr., Pennsburg, Pa.; Thomas K. Morgan, Jr., Morris Plains; Gary B. Phillips, Wharton, both of N.J.

[73] Assignee: Schering AG, Berlin, Fed. Rep. of Germany

[21] Appl. No.: 408,020

[22] Filed: Sep. 15, 1989

[51] Int. Cl.[5] .................. A61K 31/495; C07D 403/12
[52] U.S. Cl. .................... 514/252; 514/255; 544/370; 544/392; 544/393
[58] Field of Search .............. 544/370, 392, 393; 514/252, 255

[56] References Cited

U.S. PATENT DOCUMENTS 4,474,783 10/1984 Robba et al. .................. 544/358

FOREIGN PATENT DOCUMENTS 230053 7/1987 European Pat. Off. .

OTHER PUBLICATIONS

Farmaco Ed. Sci., 1984, E. Toja et al.

Primary Examiner—Jane T. Fan
Assistant Examiner—Celia Chang
Attorney, Agent, or Firm—Elizabeth A. Bellamy; John L. White; I. William Millen

[57] ABSTRACT

This invention relates to novel 2-substituted-1(4)-aryl piperazines and to a process for their preparation. The compounds of this invention have been found to have cardiovascular, primarily antiarrhythmic effects and are of the following general formula I

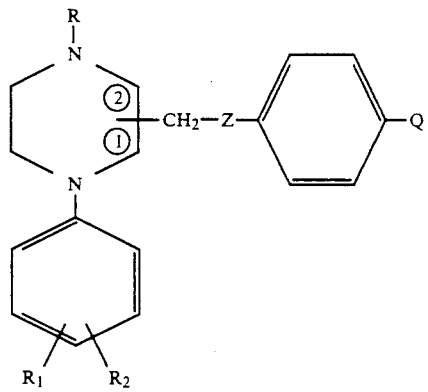

wherein R is hydrogen, lower alkyl or benzyl; and
$R_1$ and $R_2$ are the same or independently hydrogen, lower alkyl, lower alkoxy or halogen;
Z is

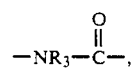

$-NR_3-CH_2-$, $-OCH_2-$, $-NR_3-$, $-O-$ or $-NR_3SO_2-$ and
Q is $(C_1-C_4)$ alkyl$-SO_2-NR_4-$ or

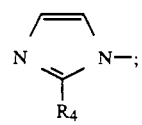

$R_3$ is hydrogen, lower alkyl, allyl or loweralkoxyloweralkyl; and
included in the descriptors of the compounds of Formula I is the proviso that when $R_4$ is methyl then

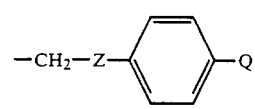

must be in the 2 position of Formula I.

17 Claims, No Drawings

2-SUBSTITUTED-1(4)-ARYL PIPERAZINES AND THE PROCESS FOR THEIR PREPARATION

FIELD OF THE INVENTION

This invention relates to novel 2-substituted-1(4)-aryl piperazines and their pharmaceutically acceptable salts. Further encompassed by the invention is a novel process for the production of the compounds. The compounds of the invention exhibit a variety of cardiovascular properties primarily of an antiarrhythmic nature for which pharmaceutical compositions are proposed.

GENERAL DESCRIPTION OF THE INVENTION

Composition-of-Matter Aspect

In its composition-of-matter aspect, this invention relates to novel 2-substituted-1(4)-aryl piperazines and the pharmaceutically acceptable salts thereof.

Compounds encompassed by the invention are of the following Formula I:

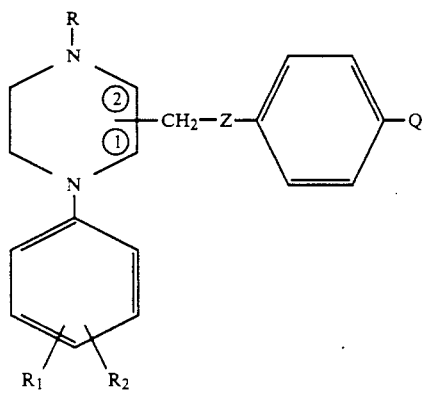

wherein R is hydrogen, lower alkyl or benzyl; and
$R_1$ and $R_2$ are the same or independently hydrogen, lower alkyl, lower alkoxy or halogen.
Z is

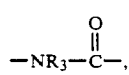

$-NR_3-CH_2-$, $-OCH_2-$, $-NR_3-$, $-O-$ or $-NR_3SO_2-$ and
Q is $(C_1-C_4)-SO_2-NR_4-$ or

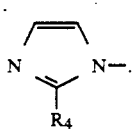

$R_3$ is hydrogen, lower alkyl, allyl or loweralkoxyloweralkyl and
$R_4$ is hydrogen or methyl.

Included in the descriptors of the compounds of Formula I is the proviso that when $R_4$ is methyl then

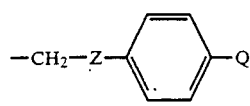

must be in the 2 position of Formula I.

As used herein, the term "lower" when used conjunctively with alkyl or alkoxy or use of the term ($C_1-C_4$) shall each represent a straight or branched chain alkyl of one to four carbon atoms as for example methyl, ethyl, propyl, isopropyl, butyl, sec-butyl, isobutyl, or tertiary butyl. The term halogen shall mean chlorine, bromine, fluorine or iodine.

Contemplated as part of this invention are the pharmaceutically acceptable salts of the compounds of Formula I. These most generally are acid in nature and formed with inorganic or organic acids. Illustrative but not restrictive examples of such acids include hydrochloric, hydrobromic, sulfuric, phosphoric, citric, acetic, propanoic, benzoic, naphthalenecarboxylic, oxalic, succinic, malic, maleic, adipic, lactic, tartaric, salicylic, methanesulfonic, 2-hydroxyethanesulfonic, toluenesulfonic, benzenesulfonic, camphorsulfonic and ethanesulfonic acids.

It is to be understood that the definition of the compounds of Formula I encompasses all possible stereoisomers and mixtures thereof which possess the activities discussed below. In particular, it encompasses the geometrical and optical isomers and the racemic modifications thereof which possess the indicated activity.

The compounds of the invention exhibit cardiovascular effects most especially antiarrhythmic effects. As antiarrhythmic agents the compounds can be classified as Class II, Class III or combination Class III/II agents.

Preferred classes of compounds which exhibit the combination Class III/II effects are those of Formula I: wherein R and $R_4$ are hydrogen and

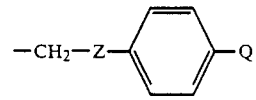

is in the ② position.

Preferred classes of compounds which primarily exhibit the Class III effect are those of Formula I wherein:
a) $R_4$ is hydrogen and

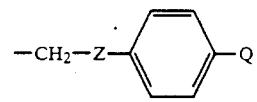

is in the ① position or
b) R is not hydrogen and $R_4$ is hydrogen.

Preferred classes of compounds which primarily exhibit the Class II effect are those of Formula I wherein R is hydrogen, $R_4$ is methyl and

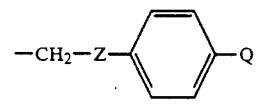

is in the ② position.

The following compounds are some of those which serve to exemplify the various composition-of-matter and/or process aspects of the invention as described herein.

1) 4-[(Methylsulfonyl)amino]-N-[[4-phenyl-1-(phenylmethyl)piperazin-2-yl]methyl]benzamide.

2) N-[4-[[[4-(3,5-Dichlorophenyl)piperazin-2-yl]methoxy]methyl]phenyl]methanesulfonamide.
3) N-[[4-(3,5-Dimethoxyphenyl)piperazin-2-yl]methyl]-4-[(ethylsulfonyl)amino]benzenesulfonamide.
4) N-[[4-(3-Bromo-5-methoxyphenyl)piperazin-2-yl]methyl]-4-(1H-imidazol-1-yl)benzenesulfonamide.
5) N-[[4-(2,6-Dichlorophenyl)piperazin-2-yl]methyl]-4-[(methylsulfonyl)amino]-N-(2-propenyl)benzenesulfonamide.
6) 4-Ethoxyphenyl-N-(2-methoxyethyl)-N-[4-(2-methyl-1H-imidazol-1-yl)phenyl]-2-piperazinemethanamine.
7) N-[[4-(3-Chlorophenyl)piperazin-2-yl]methyl]-N-methylethyl-4-[(methylsulfonyl)amino]benzamide.

Process Aspect

The novel 2-substituted-1(4)-aryl piperazines of this invention are prepared essentially as illustrated in the following Schemes A-E. These schemes are inclusive of a novel process for the regioselective preparation of an intermediate used in the process.

Scheme A

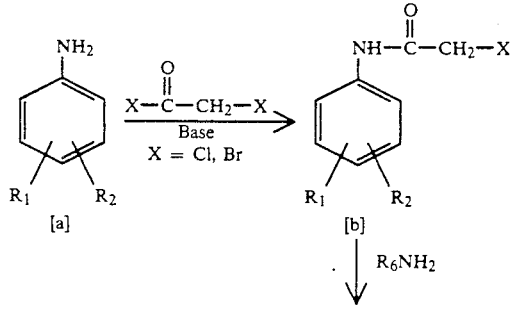

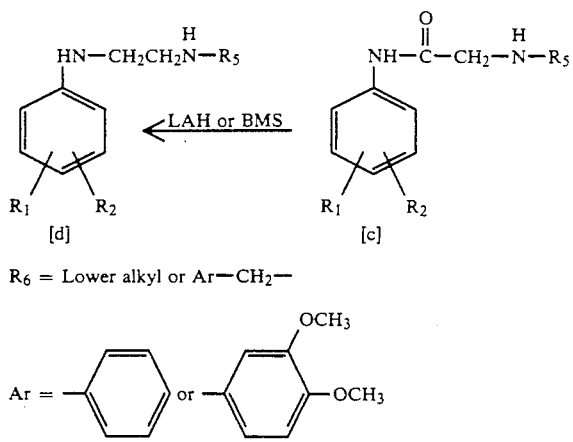

$R_6$ = Lower alkyl or Ar—$CH_2$—

Ar =

The route outlined in Scheme A illustrates the preparation of the diamines used in the process, wherein an appropriately substituted aniline [a] is reacted with a haloacetyl halide (chloride or bromide) in a solvent such as methylene chloride or acetic acid in the presence of a base such as pyridine, triethylamine or sodium acetate at a temperature of from about −20° C. to 50° C. The resulting haloacetylanilide [b] is then reacted with between two and six equivalents of a primary amine either neat or in a lower alkanol at a temperature between 20° and 120° C. to provide [c]. The compound [c] is reacted with lithium aluminum hydride or borane dimethylsulfide in an ethereal solvent at a temperature between 20° and 100° C. to provide the diamine [d]. Alternatively, the diamine [d] may be prepared by the method of Lis and Marisca (Syn. Commun. 1988, 18, 45).

Scheme B

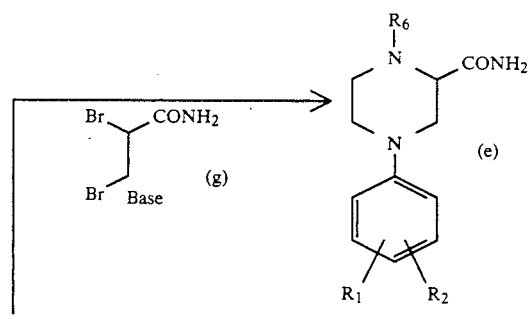

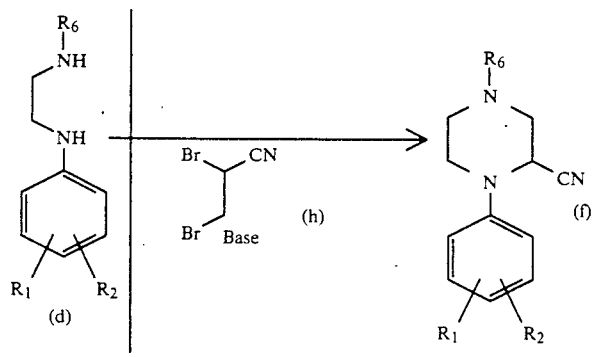

Scheme B

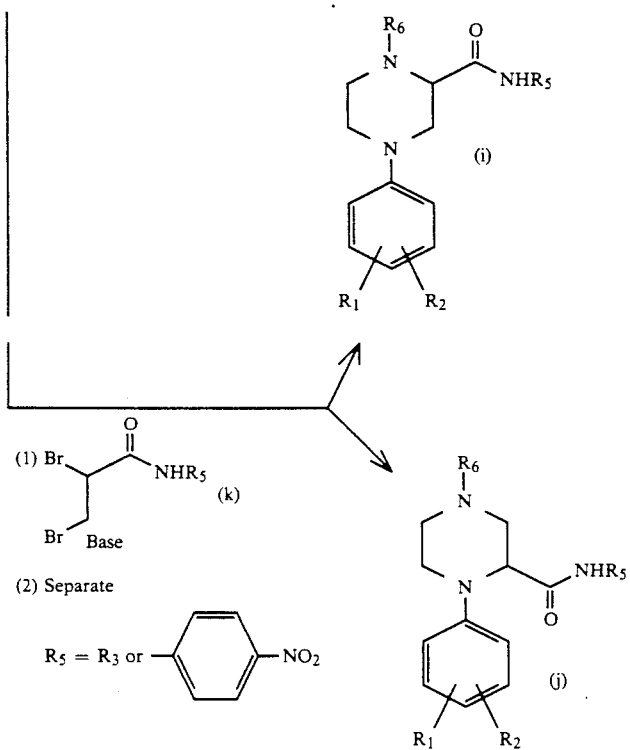

The regioselective routes outlined in Scheme B are an improvement of the method of Toja, et al. (E. Toja, A. Omodei-Sale, N. Corsico, Farmaco Ed. Sci. 1984, 39, 450) which details the reaction of N-phenyl-N'-phenylmethyl-1,2-ethanediamine with 2,3-dibromopropionic acid methyl ester to obtain a 7:3 mixture of 1-phenyl-4-phenylmethyl-2-piperazinecarboxylic acid methyl ester and 4-phenyl-1-phenylmethyl-2-piperazinecarboxylic acid methyl ester.

The route outlined in Scheme B illustrates the regioselective preparation of 4-aryl-1-(substituted)-2-piperazinecarboxamide [e] or 1-aryl-4-(substituted)-2-piperazinecarbonitrile [f]. A suitably substituted diamine [d] is combined with 2,3-dibromopropanamide [g] in a suitable solvent such as dimethylformamide, acetonitrile, or toluene in the presence of a base such as pyridine, triethylamine, or diisopropylethylamine at a temperature from about 80° to 150° C. The progress of the reaction is followed by thin-layer chromatography. Upon completion, the reaction mixture is partitioned between a suitable organic solvent (ethyl acetate, ether, or methylene chloride) and aqueous base. The organic layer is separated and dried (MgSO$_4$, Na$_2$SO$_4$, or CaSO$_4$) and evaporated. Purification by recrystallization or flash chromatography provides the amide [e]. The nitrile [f] may be prepared in an analogous fashion by using 2,3-dibromopropancarbonitrile [h] or 2-chloroacrylonitrile. The amides [i and j] may be prepared in an analogous fashion by using the appropriately substituted amide [k] and separating the two regioisomers by either recrystallization or chromatography.

Scheme C

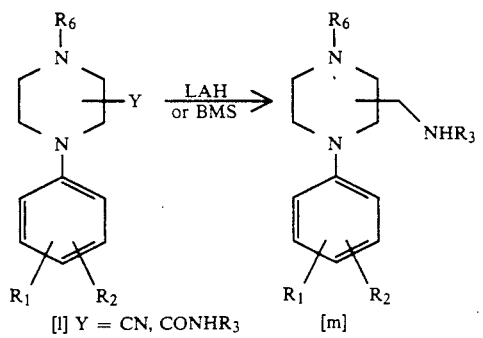

Scheme C

-continued

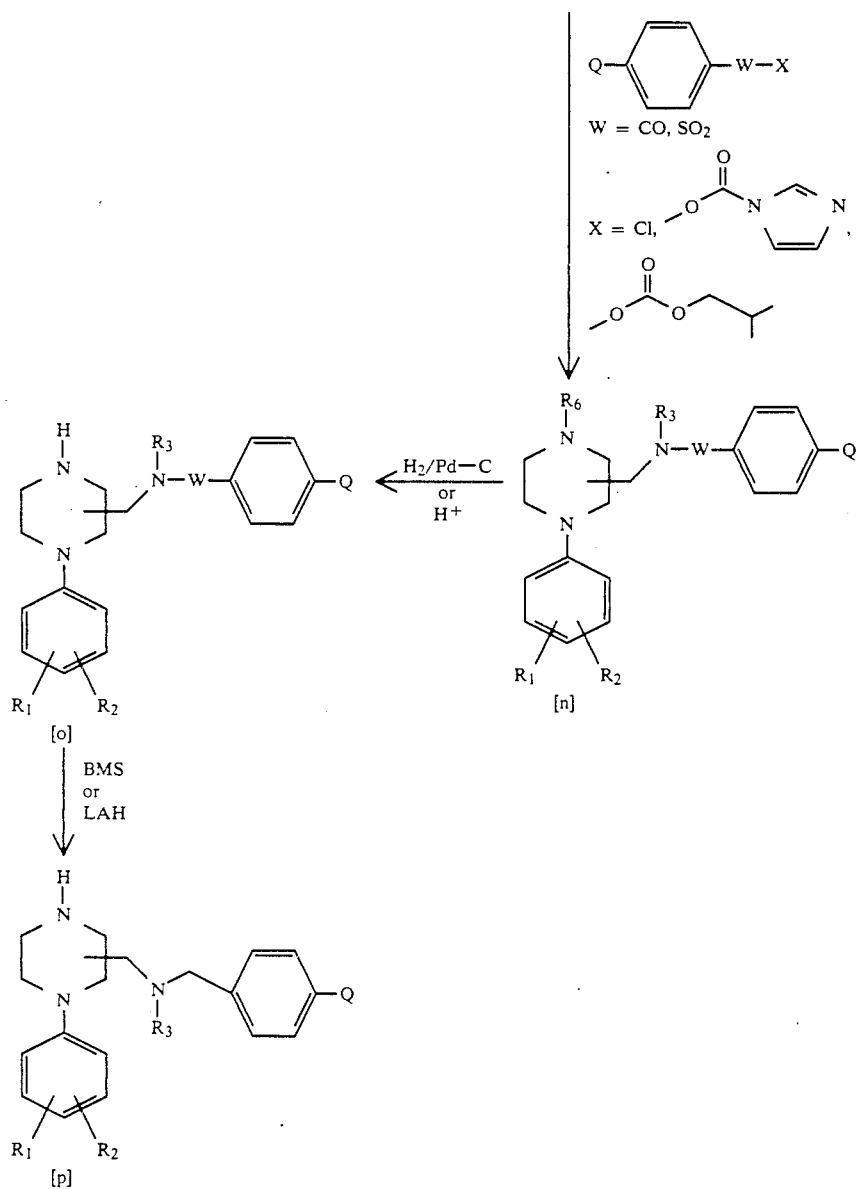

The route in Scheme C illustrates the preparation of the compounds of the invention wherein Z is NR$_3$CO, NR$_3$SO$_2$, NR$_3$CH$_2$. An appropriately substituted piperazine [l] is reacted with lithium aluminum hydride or borane dimethylsulfide in an ethereal solvent at a temperature between 20° and 100° to provide the 2-piperazinemethanamine [m]. This compound is then reacted with the appropriate activated acid to provide [n]. The typical activated acids used are acid chlorides and mixed anhydrides. An alternate route to [n] is to react the appropriate amine with trimethylaluminum followed by the appropriate methyl ester per Weinreb (Tetrahedron Lett. 1977, 4171). The benzyl group is removed in a manner according to the art and compound involved. For compounds in which hydrogenolysis is acceptable, the typical conditions are hydrogenation over palladium hydroxide or palladium on carbon in the presence of acid at 30–50 psi of hydrogen to provide [o]. For removal of a 3,4-dimethoxybenzyl group, reaction of [n] with aqueous acid (sulfuric acid, hydrobromic acid, trifluoroacetic acid, and/or acetic acid) at temperatures between 40° and 150° C. provides [o]. The benzamide [o] is converted to the amine [p] by reduction with lithium aluminum hydride or borane dimethylsulfide as described earlier.

Scheme D

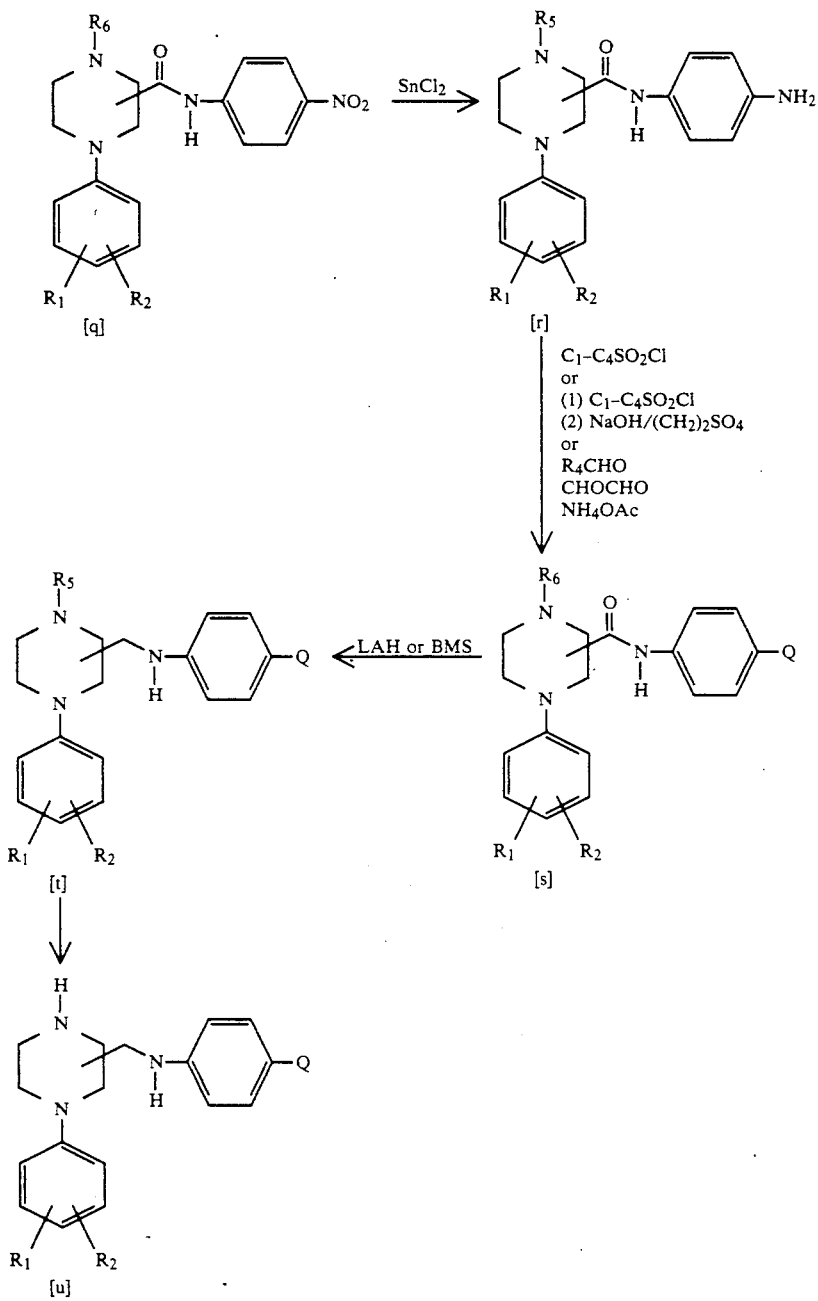

The route in Scheme D illustrates the preparation of the compounds of the invention wherein Z is NH. Reduction of the nitro group in an appropriately substituted 2-piperazinecarboxamide [q] with stannous chloride in a solvent such as ethanol or ethyl acetate at a temperature between 30°–100° C. gives the corresponding aniline [r]. Conversion of this aniline to the various groups described in the invention are as follows. To obtain an imidazole the aniline is reacted with ammonium acetate, aqueous glyoxal, and the appropriate aldehyde per the conditions of Debus (ANN. 1858, 107, 204). To obtain a sulfonamide the aniline is reacted with the appropriate alkylsulfonyl chloride or alkylsulfonic anhydride in a solvent such as acetonitrile, propionitrile, or methylene chloride at a temperature of 0°–80° C. To obtain a sulfonamide in which $R_4$ is methyl, the appropriate sulfonamide is reacted with a base such as sodium hydroxide, sodium methoxide or potassium t-butoxide and a methylating agent such as iodomethane or dimethylsulfate in an alkanol at a temperature of 0°–100° C. Reaction of the resulting amide [s] as described in Scheme C provides compounds of the invention [u].

Scheme E

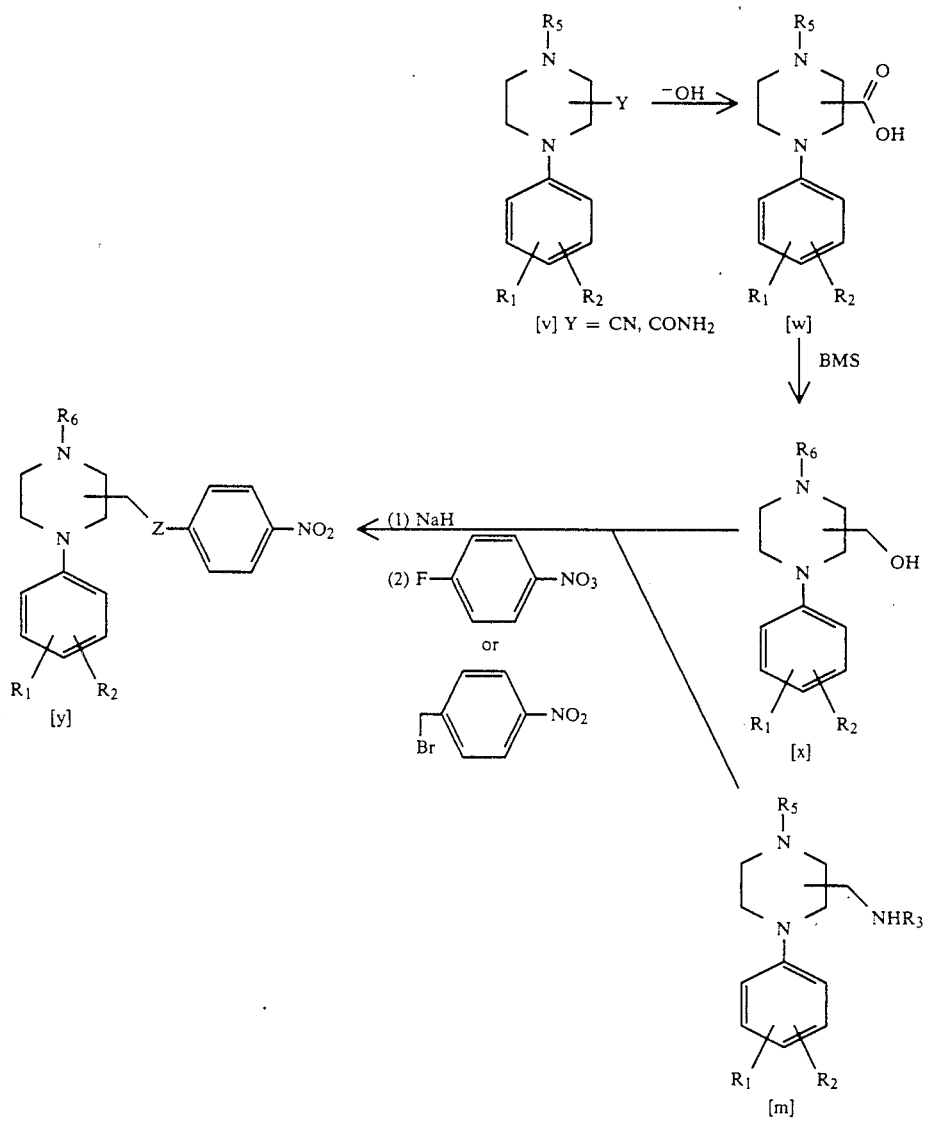

The route in Scheme E illustrates the preparation of the compounds of the invention wherein Z is —O—, —OCH$_2$—, —NR$_3$CH$_2$—, and —NR$_3$—. Hydrolysis of the amide or nitrile [v] under standard conditions provides the acid [w]. Reduction of the acid under the conditions of Brown using borane dimethylsulfide provides the alcohol [x]. Reaction of the alcohol [x] with sodium hydride and 4-fluoronitrobenzene or 4-nitrobenzyl bromide in a solvent such as toluene, dimethylformamide, or dimethylsulfoxide at a temperature between 0°-100° provides the corresponding ethers ([y], Z=O or OCH$_2$). Reaction of the amine [m] in an analogous manner provides the tertiary amines ([y], Z=NR$_3$ or NR$_3$CH$_2$). Reaction of the resulting compound [y] in a manner as described in Scheme D provides compounds of the invention.

Compounds of the invention contain asymmetric carbon atoms and may be prepared as their optically active or racemic components. Preparation of the enantiomers may be accomplished where necessary by resolution of the racemate using an optically active acid such as (+) or (−) tartaric acid, (+) or (−) camphorsulfonic acid, etc. or by resolution of an intermediate in a similar manner followed by the completion of the synthesis.

Method-of-Use and Pharmaceutical Composition Aspect

The novel 2-substituted-1(4)-aryl piperazines of this invention and their pharmaceutically acceptable salts are cardiovascular agents particularly antiarrhythmic agents. Most especially within the aegis of cardiovascular pharmacology some of the compounds are designed to provide a combination beta-adrenergic blockade with electrophysiologic activity to selectively prolong cellular refractoriness. According to the Vaughan Williams classification, such agents would have combination Class II/Class III antiarrhythmic effect. Such combination contains those therapeutic effects attributed to Class II and Class III antiarrhythmic agents singly. Other compounds of the invention demonstrate Class II or Class III antiarrhythmic effects alone.

In the Vaughan Williams classification of antiarrhythmic agents, Class II agents are the anti-adrenergic agents, among these are the so called β-blockers which decrease the sensitivity of the cardiac tissue to catecholamines. The catecholamines in excess can cause electrical instability of the heart. Class II agents are exemplified by propranolol, metoprolol, nadolol, timolol, atenolol, acebutolol and nipradilol. The Class III agents prolong the action potential duration of the heart thus increasing the time interval in which the heart is unexcitable (refractory period) without slowing conduction or changing the excitability of the cardiac cells. These agents have little or no effect on conduction, in fact, they are quite independent of conduction. Such agents are exemplified in the literature by bretylium, amiodarone, clofilium, melperone and sematilide (the latter compound developed in these laboratories).

Several investigators have demonstrated that the arrhythmia responsible for sudden cardiac death is ventricular fibrillation (VF). VF has been shown to occur via a reentrant mechanism. Reentrant ventricular arrhythmias can occur as a result of abnormalities in conduction and/or refractoriness. In a reentrant arrhythmia, a single cardiac impulse follows a circular pathway, allowing repeated excitation of the same tissue. One aproach to the abolition of such reentrant arrhythmias is to further prolong the refractory period of cardiac cells, such that the impulse, upon returning to its point of origin, is met with refractory tissue and propagation of the impulse is stopped. This is clearly the therapeutic rationale behind the development of agents possessing Class III activity.

Reentrant arrhythmias often are initiated or "triggered" by an appropriately timed premature impulse. In patients, who have had a myocardial infarction, excessive catecholamine levels may be responsible for triggering many arrhythmias which may be associated with sudden cardiac death. In fact, the results of several large, multi-center trials have shown that beta-adrenergic blockers can reduce mortality from sudden cardiac death in post-infarction patients. Presumably, beta-blockers work by decreasing the sensitivity of the heart to catecholamines, and thereby decrease the potential "triggering" event which leads to reentrant ventricular arrhythmias. The overall decrease in mortality from these studies is approximately 25%, suggesting that beta-adrenergic blockade when used alone offers no beneficial antiarrhythmic effect in the remaining majority of post-infarction patients. Clinical data such as these highlight the multiple etiologies present in patients dying of sudden cardiac death and the need for a more "broad spectrum" approach.

One broad spectrum approach is to produce an agent with both Class II and Class III properties. Several investigators have shown that an increase in sympathetic tone to the heart will shorten refractoriness, an action which can be blocked by beta-adrenergic antagonists. Preliminary data using the selective Class III agent clofilium have shown that its Class III actions are blunted in the setting of enhanced sympathetic tone (Sullivan and Steinberg, 1981). Furthermore preliminary studies performed in conscious dogs in these laboratories suggest a synergistic effect between inhibition of beta-receptors and prolongation of refractoriness. In pilot studies utilizing programmed electrical stimulation (PES) techniques to induce reentrant arrhythmias, a sub-therapeutic dose of sematilide, a Class III agent, was administered and shown not to be efficacious. Subsequent administration of a beta-blocking dose of propranolol (0.5 mg/kg, i.v.) was shown to protect the heart from PES-induced arrhythmias. Previous studies in these laboratories have demonstrated that propranolol when used alone is not efficacious in this model. In animals receiving the combination therapy, ventricular refractory period increased 8% following sematilide and 18% with the addition of propranolol. Propranolol, when used alone at this dose, had no effect on refractoriness. These data suggest a synergistic action between Class III and Class II agents and that modulation of beta-adrenergic tone can enhance the Class III properties of certain agents.

Sotalol can be considered the prototype drug for agents with both Class II and Class III activity. Experimental and clinical data suggest that the beta-blocking effect of sotalol begins at doses lower or equivalent to doses which produce its Class III actions. Thus, certain of the compounds of this invention are designed to have a more potent Class III action relative to their Class II potency in order to demonstrate a distinct advantage in the setting of reentrant ventricular arrhythmias.

The compounds of this invention have been tested for their Class III activity via in vitro electrophysiologic testing utilizing standard intracellular microelectrode techniques in the canine cardiac Purkinje fiber. They were then tested for reasonable beta-adrenergic blocking activity as measured in the in vitro screens of isolated papillary muscle (inhibition of the inotropic response to epinephrine) and the beta-adrenergic binding screen (displacement of radiolabelled dihydroalprenolol). They were then assessed in the in vivo model of the pentobarbital anesthetized dog in which the compound was administered intravenously and its Class III (increase in functional refractory period) and Class II (inhibition of isoproterenol response) effects were monitored.

The compounds of this invention exemplified by 4-[(methylsulfonyl)amino]-N-[(4-phenylpiperazin-2-yl)methyl]benzamide, N-[[4-(3-chlorophenyl)piperazin-2-yl]methyl]-4-[(methylsulfonyl)amino]benzamide, N-[4-[[[(4-phenylpiperazin-2-yl)methyl]amino]methyl]phenyl]methanesulfonamide, N-[4-[[(4-phenylpiperazin-2-yl)methyl]amino]phenyl]methanesulfonamide, N-[[4-(3-methoxyphenyl)piperazin-2-yl]methyl]-4-[(methylsulfonyl)amino]benzamide have been analyzed in the foregoing biological procedures and provide the combination Class II/III antiarrhythmic effects.

In essence the compounds of this invention provide the physician with a single chemical entity providing two effects thereby mitigating the problems of multiple drug therapy, e.g. side effects, metabolic problems, drug interactions, etc. and the problems in patient compliance—different drugs, different therapeutic regimens.

Other compounds of the invention exemplified by 4-[(methylsulfonyl)amino]-N-[(1-phenylpiperazin-2-yl)methyl]benzamide and N-[4-[[(1-phenylpiperazin-2-yl)methyl]amino]phenyl]methanesulfonamide have been analyzed in the foregoing biological procedures and provide Class III antiarrhythmic effects.

Still another group of compounds exemplified by 4-[(methyl)(methylsulfonyl)amino]-N-[(4-phenylpiperazin-2-yl)methyl]benzamide has been analyzed in the foregoing biological procedures and provides the Class II antiarrhythmic effect.

Thus, the compounds of the invention are preferably utilized in the treatment of mammalian arrhythmias and most specifically used in the treatment of mammalian arrhythmias in need of combination Class II/III effects, albeit some of the compounds may have Class II or Class III effects alone.

In general, the compounds of this invention may be administered orally or parenterally. The dosage administered will depend on the subject being treated, the route of administration and the type and severity of the arrhythmias being prevented or reduced.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. Such a capsule may contain one of the compounds of this invention, for example, 4-[(methylsulfonyl)amino]-N-[(4-phenylpiperazin-2-yl)methyl]benzamide in the amount of about 1 to about 500 mg. Such formulation can be administered orally at the rate of about 1 to 4 capsules per day or more often as needed, depending upon the particular condition and subject being treated.

For parenteral administration a compound of this invention can be formulated as an intramuscular or intravenous medicament but is not limited thereto. In the case of treatment of a patient suffering from severe cardiac arrhythmias, it may be desirable to administer a compound of the invention by intravenous slow bolus in order to effect a rapid conversion to a normal sinus rhythm. The normalized condition can then be maintained by oral administration.

The compounds of this invention can be formulated for parenteral administration with any of a number of pharmaceutically acceptable carriers and diluents to constitute an injectable liquid solution. Commonly used diluents and carriers include water or a saline solution, buffered aqueous solutions as well as dispersing and surface active agents if necessary. A typical formulation suited to intravenous or intramuscular administration may contain one of the compounds of this invention such as 4-[(methylsulfonyl)amino]-N-[(4-phenylpiperazin-2-yl)methyl]benzamide in the amount of about 50 to 150 mg and a solubilizing agent and sufficient sterile water to bring the volume to about 5 mL–100 mL. Such formulation can be infused at a constant rate or injected one to four times per day or more often depending upon the particular condition of the subject being treated.

It is further contemplated that the compounds of this invention may be formulated into sublingual lozenges or impregnated into fabric appliques for transdermal application.

The invention described hereinabove is illustrated below in the Preparations and Examples, which, however, are not to be construed as limiting the scope of this invention.

PREPARATIONS

Preparation 1

4-Phenyl-1-(phenylmethyl)-2-piperazinecarboxamide

To dimethylformamide (300 mL) add N-phenyl-N'-phenylmethyl-1,2-ethanediamine (83 g, 0.37 mol), 2,3-dibromopropanamide (90 g, 0.39 mol) and triethylamine (41 g, 0.40 mol). Heat the resulting mixture at 110° C. and follow the progress of the reaction by thin-layer chromatography. Upon completion of the reaction add 1N NaOH until basic and add ethyl ether. Filter the precipitate that forms and recrystallize from 2-propanol to obtain the title compound.

NMR (CDCl$_3$): $\delta$=2.45(m,1), 2.92(m,1), 3.10(dd,1), 3.28(dd,1), 3.40(m, 2), 3.75(m, 1), 3.99(d,1), 5.70(br s,1), 6.90(m,4) and 7.32(m,7)ppm.

Preparation 2

4-Phenyl-1-(phenylmethyl)-2-piperazinemethanamine

To 4-phenyl-1-(phenylmethyl)-2-piperazinecarboxamide (28.5 g, 96 mmol) dissolved in tetrahydrofuran (220 mL) add lithium aluminum hydride (9.0 g, 0.24 mol) portionwise. Stir and heat the reaction to reflux. Monitor the progress of the reaction by thin-layer chromatography. Upon completion, slowly add water (9 mL), 2N NaOH (9 ml), and H$_2$O (27 mL). Suction filter the slurry through celite and wash the pad with ethyl acetate (500 mL). Remove the solvent in vacuo to give a brown oil. Flash chromatograph the oil on silica (400 g) with 19/1 CH$_2$Cl$_2$/MeOH to give the title compound.

NMR (CDCl$_3$): $\delta$=2.4(m,1), 2.6(m,1), 2.9(m,3), 3.05(dd,1), 3.15(dd,1), 3.3(m,1), 3.35(d,1), 3.45(d,1), 4.1(d,1), 6.85(t,1), 6.95(d,2) and 7.2–7.4(m,7) ppm.

Preparation 3

4-[(Methylsulfonyl)amino]-N-[[4-phenyl-1-(phenylmethyl)piperazin-2-yl]-benzamide hydrochloride To tetrahydrofuran (100 mL) under nitrogen atmosphere add 4-phenyl-1-(phenylmethyl)-2-piperazinemethanamine (10 g, 35 mmol) followed by 4-[(methylsulfonyl)amino]benzoyl chloride (6.6 g, 28 mmol). When the additions are complete allow the reaction to stir. Monitor the progress of the reaction by thin-layer chromatography. Upon completion of the reaction, filter the resulting solid and wash the solid with tetrahydrofuran to give the title compound.

NMR (DMSO-d$_6$): $\delta$=3.08(s,3), 3.10–3.66(m,5), 3.71(d,1), 3.85–4.10(m,3), 4.32(m,1), 5.15(d,1), 6.88(t,1), 7.00(d,2), 7.28(m,4), 7.39(m,3), 7.70(m,2), 7.95(m,2), 9.02(m,1), 10.22(s,1) and 10.98(br s,1) ppm.

Preparation 4

1-Phenyl-4-(phenylmethyl)-2-piperazinecarbonitrile

In a manner similar to Preparation 1, react N-phenyl-N'-(phenylmethyl)-1,2-ethanediamine (0.41 g, 1.8 mmol) with 2,3-dibromopropanenitrile (0.77 g, 3.6 mmol) in toluene (5 mL) with triethylamine (0.73 g, 0.72 mmol) to obtain the title compound.

NMR (CDCl$_3$): $\delta$=2.40(dt,1), 2.55(dd,1), 3.0(d,1), 3.15(dt,1), 3.3(dt,1), 3.40(d,1), 3.60(d,1), 3.75(d,1), 4.53(br s,1), 7.0(m,3) and 7.3(m,7) ppm.

Preparation 5

1-Phenyl-4-(phenylmethyl)-2-piperazinemethanamine

In a manner similar to Preparation 2, react 1-phenyl-4-(phenylmethyl)-2-piperazinecarbonitrile (16.6 g, 60 mmol) with lithium aluminum hydride (6.8 g, 180 mmol) to obtain the title compound.

NMR (CDCl$_3$): $\delta$=2.3(m,2), 2.8(m,3), 3.1(m,2), 3.3(m,1), 3.48(d,1), 3.60(d,1), 3.7(m,1), 6.8(m,2), 6.90(d,3) and 7.3(m,7) ppm.

Preparation 6

4-[(Methylsulfonyl)amino]-N-[[1-phenyl-4-(phenylmethyl)piperazin-2-yl]methyl] benzamide In a manner similar to Preparation 3, react 1-phenyl-4-(phenylmethyl)-2-piperazinemethanamine (11.1 g, 40 mmol) with 4-[(methylsulfonyl)amino]benzoyl chloride (10.1 g, 43 mmol) to obtain the title compound.

NMR (DMSO-$d_6$): δ=2.14(m,2), 2.88(m,2), 3.05(s,3), 3.15(m,1), 3.42(m,2), 3.52(s,2), 3.69(m,1), 4.15(br s,1), 6.65(t,1), 6.95(d,2), 7.18(m,5), 7.31(t,2), 7.38(d,2), 7.62(d,2), 8.23(br t,1) and 10.08(s,1).

Preparation 7

4-(1H-Imidazol-1-yl)-N-[[4-phenyl-1-(phenylmethyl)-piperazin-2-yl]-methyl]benzamide, [RS]

To N,N-dimethylformamide (200 mL) under nitrogen atmosphere add 4-(1H-imidazol-1-yl)benzoic acid (7.0 g, 37 mmol) and 1,1-carbonyldiimidazole (6.0 g, 37 mmol) and stir for 1 h. Add 4-phenyl-1-(phenylmethyl)-2-piperazinemethanamine (9.5 g, 34 mmol) and stir. Monitor the progress of the reaction by thin-layer chromatography. Upon completion of the reaction remove the solvent in vacuo. To the oil add water (100 mL), a saturated solution of sodium bicarbonate (30 mL) and methylene chloride (200 mL) and stir for 1 h. Separate the layers and extract the aqueous layer with methylene chloride. Concentrate the combined organic layers to give an oil. Flash chromatograph the oil on silica (1000 g) with a mixture of methylene chloride, methanol, triethylamine (97/2/1). Combine and concentrate the fractions containing product. Recrystallize the solid from ethyl acetate/hexane to provide the title compound.

NMR (CDCl$_3$): δ=2.50(m,1), 2.88-3.13(m,4), 3.35(m,1), 3.51(m,2), 3.79(br s,2), 4.10(d,1), ca. 6.6-8.2(br,1), 6.82-7.02(m,4), 7.20-7.40(m,8), 7.45(d,2), 7.83(d,2) and 7.92(s,1) ppm.

Preparation 8

N-(3-Methoxyphenyl)-N'-(phenylmethyl)-1,2-ethanediamine hydrochloride

Combine 3-methoxybenzenamine (81.2 g, 0.66 mol) with N-(2-chloroethyl)-benzenemethanamine hydrochloride (45.3 g, 0.22 mol) and heat to 190° C. for 13 h. Add methylene chloride to precipitate a solid. Filter the solid and wash with methylene chloride. Triturate the solid with 100 mL of ethanol, filter the solid and wash with ethanol to give the title compound.

NMR (DMSO-$d_6$): δ=3.01(br s,2), 3.32(s,2), 3.62(s,3), 4.14(br s,2), 5.88-6.25(m,3), 6.95(t,1), 7.25-7.50(m,3), 7.58(s,2) and 9.3(br s,2) ppm.

Preparation 9

4-(3-Methoxyphenyl)-1-(phenylmethyl)-2-piperazinecarboxamide

In a manner similar to Preparation 1, react N-(3-methoxyphenyl)-N'-(phenylmethyl)-1,2-ethanediamine (16 g, 63 mmol) with 2,3-dibromopropanamide (29 g, 126 mmol) and triethylamine (25 g, 0.25 mol) to give the title compound.

NMR (CDCl$_3$): δ=2.4(m,1), 2.94(m,2), 3.07(dd,1), 3.25(dd,1), 3.38(m,2), 3.75(m,1), 3.78(s,3), 3.98(d,1), 5.8(s,1), 6.45(m,2), 6.54(d,1), 7.0(s,1), 7.17(t,1) and 7.3(m,5) ppm.

Preparation 10

4-(3-Methoxyphenyl)-1-(phenylmethyl)-2-piperazinemethanamine

In a manner similar to Preparation 2, react 4-(3-methoxyphenyl)-1-(phenylmethyl)-2-piperazinecarboxamide (0.9 g, 27 mmol) with lithium aluminum hydride (2.1 g, 55 mmol) to give the title compound.

NMR (CDCl$_3$): δ=2.4(m,1), 2.6(m,1), 2.9(m,3), 3.05(dd,1), 3.15(dd,1), 3.31(m,1), 3.35(d,1), 3.45(d,1), 3.72(s,3), 4.1(d,1), 6.32-6.66(m,3), and 7.00-7.46(m,6) ppm.

Preparation 11

4-[(Methylsulfonyl)amino]-N-[[4-(3-methoxyphenyl)-1-(phenylmethyl)piperazin-2-yl]methyl]benzamide dihydrochloride In a manner similar to Preparation 3, react 4-(3-methoxyphenyl)-1-(phenylmethyl)-2-piperazinemethanamine (3.1 g, 10 mmol) with 4-[(methylsulfonyl)amino]benzoyl chloride (3.3 g, 15 mmol) to obtain the title compound.

NMR (DMSO-$d_6$): δ=3.08(s,3), 3.10-3.66(m,5), 3.70(s,3), 3.71(d,1), 3.85-4.10(m,3), 4.32(m,1), 5.15(d,1), 6.40-6.62(m,3), 7.18(t,1), 7.31(d,2), 7.49(m,3), 7.74(m,2), 8.00(d,2) and 10.24(s,1) ppm.

Preparation 12

N-(2-Methoxyphenyl)-2-[(phenylmethyl)amino]acetamide

To ethanol (100 mL) add benzylamine (35 g, 0.33 mol) and 2-chloro-N-(2-methoxyphenyl)acetamide (22 g, 0.11 mol). Stir and heat the reaction at 50° C. Monitor the progress of the reaction by thin-layer chromatography. Upon completion of the reaction remove the precipitate that has formed by suction filtration and discard. Evaporate the filtrate and partition the residue between ethyl acetate and 2N NaOH(aq). Separate the organic layer and dry it over Na$_2$SO$_4$. Remove the drying agent by filtration and remove the solvent in vacuo. Chromatograph the residue on silica gel (400 g) using hexane/EtOAc (3/1) as eluent to obtain the title compound.

NMR (CDCl$_3$): δ=3.43(s,2), 3.82(s,2), 3.88(s,3), 6.88(dd,1), 6.95(t,1), 7.04(t,1), 7.2-7.4(m,6), 8.44(dd,1) and 9.9(br s,1) ppm.

Preparation 13

N-(2-Methoxyphenyl)-N'-(phenylmethyl)-1,2-ethanediamine

In a manner similar to Preparation 2, react N-(2-methoxyphenyl)-2-[(phenylmethyl)amino]acetamide (0.31 g, 1.1 mmol) with lithium aluminum hydride (0.09 g, 2.4 mmol) to obtain the title compound.

NMR (CDCl$_3$): δ=2.85(t,2), 3.2(t,2), 3.75(s,2), 3.8(s,3), 4.6(br,1), 6.6(d,1), 6.65(m,1), 6.75(d,1), 6.85(t,1), and 7.2-7.4(m,5) ppm.

Preparation 14

4-(2-Methoxyphenyl)-1-(phenylmethyl)-2-piperazinecarboxamide

In a manner similar to Preparation 1, react N-(2-methoxyphenyl)-N'-(phenylmethyl)-1,2-ethanediamine (15.4 g, 60.2 mmol) with 2,3-dibromopropanamide (27.7 g, 0.12 mol) to give the title compound.

NMR (CDCl$_3$): δ=2.61(m,1), 2.92(m,2), 3.05(dd,1), 3.2(m,1), 3.38(m,1), 3.45(m,1), 3.61(d,1), 3.85(d,1), 3.85(s,3), 5.6(br,1), 6.87(d,1), 6.95(m,2), 7.05(m,1), 7.3(m,5), and 7.6(br,1) ppm.

Preparation 15

4-(2-Methoxyphenyl)-1-(phenylmethyl)-2-piperazinemethanamine

In a manner similar to Preparation 2, react 4-(2-methoxyphenyl)-1-(phenylmethyl)-2-piperazinecarboxamide (4.0 g, 16.6 mmol) with lithium aluminum hydride (1.0 g, 26 mmol) to give the title compound.

NMR (CDCl$_3$): $\delta$=2.5(t,1), 2.65(m,1), 2.75(t,1), 2.9(m,2), 3.0(dd,1), 3.2(m,3), 3.4(d,1), 3.85(s,3), 4.1(d,1), 6.8–7.0(m,4) and 7.2–7.4(m,5) ppm.

Preparation 16

N-[[4-(2-Methoxyphenyl)-1-(phenylmethyl)piperazin-2-yl]methyl]-4-[(methylsulfonyl)amino]benzamide hydrochloride In a manner similar to Preparation 3, react 4-(2-methoxyphenyl)-1-(phenylmethyl)-2-piperazinemethanamine (3.8 g, 12 mmol) with 4-[(methylsulfonyl)amino]benzoyl chloride (3.2 g, 14 mmol) to give the title compound.

NMR (DMSO-d$_6$): $\delta$=3.08(s,3), 3.0–3.2(m,3), 3.4–3.9(m,5), 3.7(s,3), 4.05(m,1), 4.3(m,1), 5.1(d,1), 6.9–7.1(m,4), 7.3(d,2), 7.5(s,4), 7.75(m,2), 7.95(d,2), 9.0(br,1), 10.2(s,1) and 11.05(br,1) ppm.

Preparation 17

4-Phenyl-1-(phenylmethyl)-2-piperazinecarboxylic acid

Suspend 4-phenyl-1-(phenylmethyl)-2-piperazinecarboxamide (14.5 g, 49 mmol) in ethylene glycol (400 mL) and add potassium hydroxide (27.5 g, 490 mmol). Heat this mixture to 150° C. for 18 h. After this time, remove the solvent in vacuo. Add 6M hydrochloric acid (81.5 mL, 0.49 mol) and water (300 mL) and filter the resultant solid to obtain the title compound.

NMR (DMSO-d$_6$): $\delta$=2.78(m,1), 3.28(m,3), 3.56(m,2), 3.70(m,1), 3.98(d,1), 4.24(d,1), 4.3–6.6(br,1), 6.83(t,1), 6.92(d,2) and 7.15–7.55(m,7) ppm.

Preparation 18

4-Phenyl-1-(phenylmethyl)-2-piperazinemethanol

Suspend 4-phenyl-1-(phenylmethyl)-2-piperizinemethanol (12.2 g, 41 mmol) in tetrahydrofuran (800 mL) and add borane methylsulfide (12.4 mL, 124 mmol) dropwise over 30 minutes under nitrogen. Stir and heat the reaction to reflux and distill off 50 mL of liquid. Continue refluxing this mixture for 3 h. After this time, cool to room temperature and add methanol (100 mL). Allow the reaction mixture to stand at room temperature for 2 h. After this time, remove the solvent in vacuo. Add ethyl acetate (800 mL) and 1N sodium hydroxide (200 mL) and enough methanol to clarify the solution. Separate the layers, then wash the organic layer with water (200 mL) and remove the solvent in vacuo. Flash chromatograph the residue on flash silica gel with acetonitrile to give the title compound.

NMR (DMSO-d$_6$): $\delta$=2.27(m,1), 2.55(m,1), 2.68–2.86(m,3), 3.23–3.58(m,4), 3.79(m,1), 4.10(dd,1), 4.71(m,1), 6.75(m,1), 6.90(d,2) and 7.14–7.39(m,7) ppm.

Preparation 19

2-[(4-Nitrophenoxy)methyl]-4-phenyl-1-(phenylmethyl)piperazine

Suspend 4-phenyl-1-(phenylmethyl)-2-piperazinemethanol (7.8 g, 27.6 mmol) in dimethylformamide under nitrogen and add 60% sodium hydride (1.22 g, 30.4 mmol). Stir for 20 h as solid slowly dissolves. Add 1-fluoro-4-nitrobenzene (4.29 g, 30.4 mmol) and stir at room temperature. Monitor the progress of the reaction by thin-layer chromatography. Upon completion of the reaction, add water (100 mL) to the reaction mixture and extract with methylene chloride (2×100 mL). Remove the solvent in vacuo and recrystallize the residue from ethyl acetate/hexanes (1/1) (80 mL) to provide the title compound.

NMR (DMSO-d$_6$): $\delta$2.47(m,1), 2.84(m,1), 3.05(m,1), 3.20(m,1), 3.45(m,1), 3.56(d,1), 4.05(d,1), 4.36(m,1), 4.51(m,1), 6.75(t,1), 6.93(d,2), 7.12–7.43(m,9) and 8.19(d,2) ppm.

Preparation 20

4-[[4-Phenyl-1-(phenylmethyl)piperazin-2-yl]methoxy]benzeneamine

Dissolve 2-[(4-nitrophenoxy)methyl]-4-phenyl-1-(phenylmethyl)piperazine (7.15 g, 17.7 mmol) in a 1/1 mixture of methanol and ethyl acetate (350 mL) and add tin II chloride dihydrate (20.0 g, 88.6 mmol). Stir the mixture and heat the reaction to reflux. Monitor the progress of the reaction by thin-layer chromatography and add more tin II chloride dihydrate as needed. Upon completion of the reaction, pour reaction mixture into water (200 mL) and add 4N sodium hydroxide to pH=12. Extract with a solution of ethyl acetate/methanol (2/1) (2×200 mL). Wash the combined extracts with water (200 mL) and remove the solvent in vacuo. Flash chromatograph the residue on flash silica gel (250 g) with an ethyl acetate/hexanes [gradient (1/1–1/0)] to give the title compound.

NMR (CDCl$_3$): $\delta$=2.47(m,1), 2.87(m,1), 2.97–3.28(m,3), 3.43(br s,2), 3.55(m,1), 4.02–4.27(m,3), 6.64(d,2), 6.76(d,2), 6.84(t,1), 6.93(d,2) and 7.20–7.42(m,7) ppm.

Preparation 21

N-[4-[[4-Phenyl-1-(phenylmethyl)piperazin-2-yl]methoxy]phenyl]methanesulfonamide Dissolve 4-[[4-phenyl-1-(phenylmethyl)piperazine-2-yl]methoxy]benzeneamine (6.28 g, 16.8 mmol) in acetonitrile (100 mL) and add methanesulfonic anhydride (3.22 g, 18.5 mmol). Monitor the progress of the reaction by thin-layer chromatography. Upon completion of the reaction, add water (100 mL), ethyl acetate (50 mL) and sat. aq. sodium bicarbonate (50 mL). Separate the layers and reextract the aqueous layer with ethyl acetate (75 mL). Wash the combined organic extracts with sat. aq. sodium chloride (75 mL) and remove the solvent in vacuo to give the title compound.

NMR (DMSO-d$_6$): $\delta$2.42(m,1), 2.82(m,1), 2.89(2,3), 2.99(m,1), 3.11(m,1), 3.21(m,1), 3.52(d,1), 4.07(d,1), 4.17(m,1), 4.31(m,1), 6.77(t,1), 6.93(d,2), 6.98(d,2), 7.10–7.45(m,9) and 9.37(br s,1) ppm.

Preparation 22

2,3-Dibromo-N-(4-nitrophenyl)propanamide

To N-(4-nitrophenyl)-2-propenamide (58 g, 0.30 mol) suspended in CCl$_4$ (200 mL) at 0° C. add bromine (16.2 g, 0.317 mol) dropwise. Monitor the progress of the reaction by thin-layer chromatography. Upon completion of the reaction, filter the solid to obtain the title compound.

NMR (DMSO-d$_6$): $\delta$=3.96–4.14(m,2), 4.85(dd,1), 7.88(d,2), 8.28(d,2), and 11.20(s,1) ppm.

Preparation 23

N-(4-Nitrophenyl)-4-phenyl-1-(phenylmethyl)-2-piperazinecarboxamide (A)

and

N-(4-Nitrophenyl-1-phenyl-4-(phenylmethyl)-2-piperazinecarboxamide (B)

Add N-phenyl-N'-(phenylmethyl)-1,2-ethanediamine (29 g, 128 mmol), N-(4-nitrophenyl)-2,3-dibromopropanamide (45 g, 128 mmol) and triethylamine (36 mL, 255 mmol) to dimethylformamide (100 mL). Stir the mixture and heat the reaction to 105° C. Monitor the progress of the reaction by thin-layer chromatography. Upon completion of the reaction, add 1N NaOH until basic and add diethyl ether (2×300 mL). Filter the resulting precipitate. Add sat. aq. sodium chloride (200 mL) to aqueous layer and extract with 2-propanol (300 mL). Evaporate the solvent from the organic layer and combine the resulting residue and the initial precipitate. Flash chromatograph this mixture on flash silica gel (525 g) with an ethyl acetate/hexanes [gradient (1/3→1/1)] to give both compounds A & B.

A—NMR (DMSO-d$_6$): δ=2.38(m,1), 2.94(m,2), 3.19(dd,1), 3.36(m,2), 3.43(d,1), 3.71(d,1), 3.88(d,1), 6.79(t,1), 6.96(d,2), 7.31(m,7), 7.97(d,2), 8.25(d,2) and 10.66(s,1) ppm.

B—NMR (DMSO-d$_6$): δ=2.36(td,1), 2.44(dd,1), 2.96(d,1), 3.25(d,1), 3.42(d,1), 3.53(d,1), 3.65(m,1), 3.68(d,1), 4.54(s,1), 6.72(t,1), 6.86(d,2), 7.19(m,7), 7.50(d,2), 8.22(d,2) and 10.49(s,1) ppm.

Preparation 24

N-(4-Aminophenyl)-4-phenyl-1-(phenylmethyl)-2-piperazinecarboxamide

In a manner similar to Preparation 20, react N-(4-nitrophenyl)-4-phenyl-1-(phenylmethyl)-2-piperazinecarboxamide (6.85 g, 16.8 mmol) with tin (II) chloride dihydrate (18.5 g, 82 mmol) to obtain the title compound.

NMR (DMSO-d$_6$): δ=2.28(m,1), 2.82(m,2), 3.08(m,1), 3.18(m,1), 3.28(d,1), 3.48(m,1), 3.64(m,1), 3.86(d,2), 4.90(s,2), 6.62(d,2), 6.78(t,1), 6.94(d,2), 7.18–7.44(m,4) and 9.6(s,1) ppm.

Preparation 25

N-[4-[(Methylsulfonyl)amino]phenyl]-4-phenyl-1-(phenylmethyl)-2-piperazinecarboxamide In a manner similar to Preparation 21, react N-(4-aminophenyll)-4-phenyl-1-(phenylmethyl)-2-piperazinecarboxamide (5.88 g, 15.2 mmol) with methanesulfonic anhydride (2.91 g, 16.7 mmol) to obtain the title compound.

NMR (DMSO-d$_6$): δ=2.30(m,1), 2.86(m,2), 2.92(s,3), 3.11(t,1), 3.25(dd,1), 3.32(d,1), 3.46(d,1), 3.66(d,1), 3.86(d,1), 6.79(t,1), 6.95(d,2), 7.14–7.44(m,9), 7.63(d,2), 9.57(s,1) and 10.03(s,1) ppm.

Preparation 26

N-[4-[[[[4-Phenyl-1-(phenylmethyl)piperazin-2-yl]methyl]amino]phenyl]methanesulfonamide In a manner similar to Preparation 18, react N-[4-[(methylsulfonyl)amino]phenyl]-4-phenyl-1-(phenylmethyl)-2-piperazinecarboxamide (4.1 g, 8.8 mmol) with borane dimethylsulfide (2.65 mL of a 10N solution, 26.5 mmol) to obtain the title compound.

NMR (DMSO-d$_6$): δ=2.39(br t,1), 2.83(s,3), 2.8–3.0(m,4), 3.2–3.5(m,5), 4.13(d,1), 5.63(br s,1), 6.60(d,2), 6.80(t,1), 6.95(m,4), 7.20–7.43(m,7) and 9.00(s,1) ppm.

Preparation 27

N-[4-[(Methylsulfonyl)amino]phenyl]-1-phenyl-4-(phenylmethyl)-2-piperazinecarboxamide Dissolve N-(4-nitrophenyl)-1-phenyl-4-(phenylmethyl)-2-piperazinecarboxamide (17.7 g, 30.5 mmol) in ethyl acetate (1200 mL) and add tin II chloride dihydrate (34.4 g, 153 mmol). Stir this mixture and heat to reflux. Monitor the progress of the reaction by thin-layer chromatography and add more tin II chloride dihydrate if necessary. Upon completion of the reaction, pour the reaction mixture into crushed ice (1 kg) and neutrallize the mixture to pH=8 with sat. aq. sodium bicarbonate. Dilute with ethyl acetate (1000 mL) and filter through celite. Wash the organic layer with sat. aq. sodium chloride and remove the solvent. Flash chromatograph the residue on silica gel (350 g) with an ethyl acetate/hexanes [gradient (1/3–1/1)] to give an oil. Dissolve this oil in acetonitrile (100 mL) and add methanesulfonic ahydride (3.34 g, 19.2 mmol). Warm this mixture to 80° C. for 10 min. After this time, cool the mixture to room temperature and add sat. aq. sodium bicarbonate (100 mL) ethyl acetate (100 mL) and water (50 mL). Wash the organic layer with sat. aq. sodium chloride (100 mL) and remove the solvent in vacuo. Recrystallize the residue from ethyl acetate (100 mL) to provide the title compound.

NMR (CDCl$_3$): δ=2.55(m,1), 2.82(m,2), 2.96(s,3), 3.08(dd,1), 3.40(m,2), 3.61(dd,2), 4.33(t,1), 6.26(s,1), 6.92(t,1), 7.05(d,2), 7.13(d,2), 7.22–7.45(m,9) and 9.20(s,1) ppm.

Preparation 28

N-[4-[[[1-Phenyl-4-(phenylmethyl)piperazin-2-yl]methyl]amino]phenyl]methanesulfonamide In a manner similar to Preparation 18, react N-[4-[(methylsulfonyl)amino]phenyl]-4-phenyl-1-(phenylmethyl)-2-piperazinecarboxamide (5.88 g, 12.7 mmol) with borane dimethylsulfide (3.8 mL of a 10N solution, 38 mmol) to give the title compound.

NMR (DMSO-d$_6$): δ=2.16–3.4(m,2), 2.8(s,3), 2.8–3.05(m,3), 3.14(br t,1), 3.3–3.65(m,4), 3.92(m,1), 5.2(br s,1) 6.46(d,2), 6.72(t,1), 6.89(d,2), 6.93(d,2), 7.15–7.40(m,7) and 8.62(m,1) ppm.

Preparation 29

N-[3-[[2-[(Phenylmethyl)amino]ethyl]amino]phenyl]acetamide hydrochloride

Combine N-(3-aminophenyl)acetamide (31 g, 0.206 mol) and N-(2-chloroethyl)benzenemethanamine hydrochloride (17.0 g, 0.083 mol) and heat to 180° C. for 1 h. After this time, allow to cool to approximately 85° C. and add isopropanol (100 mL) to precipitate a solid. Decant the solvent and dissolve the white residue in refluxing methanol (800 mL). Filter hot and allow the solution to cool to room temperature. After 2 h, filter the resulting white solid and wash with methanol (50 mL) to give the title compound.

NMR (DMSO-d$_6$): δ=2.03(s,3), 3.09(br s,2), 3.40(m,2), 4.21(s,2), 5.88(br,1), 6.32(d,1), 6.76(d,1), 7.02(m,2), 7.47(m,3), 7.59(m,2), 9.33(br,2) and 9.77(s,1) ppm.

Preparation 30

4-[3-(Acetylamino)phenyl]-1-(phenylmethyl)-2-piperazinecarboxamide

In a manner similar to Preparation 1, react N-[3-[[2-[(phenylmethyl)amino]ethyl]amino]phenyl]acetamide (25.6 g, 90.4 mmol) with 2,3-dibromopropanamide (41.8 g, 180.8 mmol) to obtain the title compound.

NMR (DMSO-$d_6$): $\delta$2.03(s,3), 2.23(m,1), 2.79(m,2), 2.97(m,2), 3.23(d,1), 3.39(m,1), 3.55(d,1), 5.91(d,1), 6.63(d,1), 7.1(m,2), 7.19(s,1), 7.35(m,6), 7.55(s,1), and 9.80(s,1) ppm.

Preparation 31

4-(3-Aminophenyl)-1-(phenylmethyl)-2-piperazinecarboxamide

To 4-[3-(acetylamino)phenyl]-1-(phenylmethyl)-2-piperazinecarboxamide (14.0 g, 39.9 mmol) in methanol (115 mL) add 6N aqueous hydrochloric acid (28 mL). Stir the reaction at reflux. Monitor the progress of the reaction by thin-layer chromatography. Upon completion of the reaction adjust the pH to 12 with 4N aqueous NaOH to obtain a white precipitate. Filter the precipitate to obtain the title compound.

NMR (DMSO-$d_6$): $\delta = 2.20$(m,1), 2.74(m,2), 2.92(m,2), 3.21(d,1), 3.51(d,1), 3.89(d,1), 4.9(s,2), 6.05(d,1), 6.12(d,1), 6.16(s,1), 6.86(t,1), 7.34(m,6), and 7.50(s,1) ppm.

Preparation 32

4-(3-Aminophenyl)-1-(phenylmethyl)-2-piperazinemethanamine

In a manner similar to Preparation 18, react 4-(3-aminophenyl)-1-(phenylmethyl)-2-piperazinecarboxamide (9.0 g, 30 mmol) with borane dimethylsulfide complex (15 mL, 150 mmol) to obtain the title compound.

NMR (DMSO-$d_6$): $\delta = 2.26$(m,1), 2.38(m,1), 2.64–2.94(m,5), 3.17–3.6(m,5), 4.09(d,1), 4.86(s,2), 6.05(d,1), 6.15(d,1), 6.17(s,1), 6.85(t,1), 7.28(m,1), and 7.36(m,4) ppm.

Preparation 33

N-[[4-(3-Aminophenyl)-1-(phenylmethyl)piperazin-2-yl]methyl]-4-[(methylsulfonyl)amino]benzamide In a manner similar to Preparation 3, react 4-(3-aminophenyl)-1-(phenylmethyl)-2-piperazinemethanamine (4.8 g, 16 mmol) with 4-[(methylsulfonyl)amino]benzoyl chloride (3.8 g, 16 mmol) to obtain the title compound.

NMR (DMSO-$d_6$): $\delta = 2.33$(m,1), 2.80(m,4), 3.03–3.24(m,2), 3.08(s,3), 3.36(m,1), 3.45(d,1), 3.72(m,1), 4.16(d,1), 4.88(br s,2), 6.06(d,1), 6.14(d,1), 6.16(s,1), 6.86(t,1), 7.33(m,7), 7.87(d,2), 8.48(t,1) and 10.15(br s,1) ppm.

Preparation 34

N-[[4-[3-(1H-Imidazol-1-yl)phenyl]-1-(phenylmethyl)-piperazin-2-yl]methyl]-4-[(methylsulfonyl)amino]benzamide To reagent alcohol (60 mL) at 60° C. simultaneously add a solution of N-[[4-(3-aminophenyl)-1-(phenylmethyl)piperazin-2-yl]methyl]-4-[(methylsulfonyl)amino]benzamide (7.1 g, 14 mmol) and ammonium hydroxide (28% aqueous ammonia, 1.94 mL, 29 mmol) diluted to 200 mL with alcohol and a solution of aqueous glyoxal (1.9 mL, 17 mmol) and aqueous formaldehyde (1.6 mL, 22 mmol) diluted to 200 mL with alcohol. Upon completion of the additions, monitor the progress of the reaction by thin-layer chromatography. Upon completion of the reaction, partition the reaction between ethyl acetate and aqueous NaHCO$_3$. Separate and dry the organic layer and remove the solvent in vacuo. Flash chromatograph the residue on silica with CH$_3$CN/NH$_4$OH (99/1) to obtain the title compound.

NMR (DMSO-$d_6$): $\delta = 2.35$(m,1), 2.80(m,2), 3.08(m,5), 3.32(m,1), 3.51(m,3), 3.73(m,1), 4.13(d,1), 6.91(d,1), 7.00(d,1), 7.03(s,1), 7.32(m,10), 7.69(s,1), 7.86(d,2), 8.21(s,1) and 8.29(t,1) ppm.

Preparation 35

N-(3-Chlorophenyl)-2-[[(3,4-dimethoxyphenyl)methyl]amino]acetamide

In a manner similar to Preparation 11, react 2-bromo-N-(3-chlorophenyl)acetamide (4.4 g, 18 mmol) with 3,4-dimethoxybenzenemethanamine (8.7 g, 53 mmol) to obtain the title compound.

NMR (CDCl$_3$): $\delta = 3.40$(s,2), 3.75(s,2), 3.84(s,3), 3.86(s,3), 6.85(m,3), 7.10(d,1), 7.23(m,2), 7.42(d,2) and 7.66(s,1) ppm.

Preparation 36

N-(3-chlorophenyl)-N'-[(3,4-dimethoxyphenyl)methyl]-1,2-ethanediamine

In a manner similar to Preparation 2, react N-(3-chlorophenyl)-2-[[(3,4-dimethoxyphenyl)methyl]amino]acetamide (13.6 g, 40.1 mmol) with lithium aluminum hydride (3.1 g, 81 mmol) to obtain the title compound.

NMR (CDCl$_3$): $\delta = 2.90$(t,2), 3.22(m,2), 3.77(s,2), 3.86(s,3), 3.88(s,3), 6.41–6.70(m,3), 6.75–6.93(m,3) and 7.08(t,1) ppm.

Preparation 37

4-(3-Chlorophenyl)-1-[(3,4-dimethoxyphenyl)methyl]-2-piperazinecarboxamide

In a manner similar to Preparation 1, react N-(3-chlorophenyl)-N'-[(3,4-dimethoxyphenyl)methyl]-1,2-ethanediamine (13.3 g, 41 mmol) with 2,3-dibromopropanamide (19.1 g, 166 mmol) to obtain the title compound.

NMR (DMSO-$d_6$): $\delta = 2.20$(t,1), 2.50(s,1), 2.72–2.98(m,2), 3.06(t,1), 3.25(d,1), 3.49(m,2), 3.60(d,1), 3.75(m,6), 6.72–7.05(m,4), 7.13–7.35(m,2) and 7.52(s,1) ppm.

Preparation 38

4-(3-Chlorophenyl)-1-[(3,4-dimethoxyphenyl)methyl]-2-piperazinemethanamine

In a manner similar to Preparation 2, react 4-(3-chlorophenyl)-1-[(3,4-dimethoxyphenyl)methyl]-2-piperazinecarboxamide (6.0 g, 15 mmol) with lithium aluminum hydride (1.2 g, 31 mmol) to obtain the title compound.

NMR (CDCl$_3$): $\delta = 2.30$–2.42(m,1), 2.50–2.60(m,1), 2.85–2.96(m,3), 3.03–3.14(m,2), 3.25–3.35(m,2), 3.50(d,1), 3.90(s,6), 4.05(d,1), 6.75–6.92(m,6) and 7.15(t,1) ppm.

Preparation 39

N-[[4-(3-Chlorophenyl)-1-[(3,4-dimethoxyphenyl)methyl]piperazin-2-yl]methyl]-4-[(methylsulfonyl)amino]benzamide In a manner similar to Preparation 3, react 4-(3-chlorophenyl)-1-[(3,4-dimethoxyphenyl)methyl]-2-piperazinemethanamine (3.0 g, 7.9 mmol) with 4-[(methylsulfonyl)amino]benzoyl chloride (2.4 g, 10 mmol) to obtain the title compound.

NMR (CDCl$_3$): $\delta$=2.85–3.05(m,3), 3.10(s,3), 3.30–3.52(m,4), 3.72–3.92(m,8), 4.02(d,2), 6.75–6.92(m,6), 7.15(t,1), 7.26(d,2) and 7.70(d,2) ppm.

Preparation 40

4-[(Methyl)(methylsulfonyl)amino]-N-[[4-phenyl-1-(phenylmethyl)piperazin-2-yl]methyl]benzamide To 4-phenyl-1-(phenylmethyl)-2-piperazinemethanamine (6.95 g, 24.7 mmol) in toluene (130 mL) at 0° C. add trimethylaluminum (2.0M in toluene, 16.2 mL, 32.4 mmol). Allow the reaction to warm to room temperature and add 4-[(methyl)(methylsulfonyl)amino]benzoic acid methyl ester (6.91 g, 28.4 mmol). Heat the reaction and monitor the progress by thin-layer chromatography. Upon completion make the solution basic with aqueous NaOH and extract with EtOAc. Remove the solvent in vacuo. Flash chromatograph the residue on silica gel with EtOAc/hexane (2/1) to obtain the title compound.

NMR (DMSO-d$_6$): $\delta$=2.36(m,1), 2.81(m,2), 2.87–3.10(m,2), 3.02(s,3), 3.24(m,1), 3.31(s,3), 3.35–3.58(m,2), 3.50(d,1), 3.77(m,1), 4.16(d,1), 6.80(t,1), 6.96(d,2), 7.18–7.45–(m,7), 7.55(d,2), 7.91(d,2) and 8.62(t,1) ppm.

Preparation 41

4-(3-Aminophenyl)-2-piperazinecarboxamide

To methanol add 4-(3-aminophenyl)-1-(phenylmethyl)-2-piperazinecarboxamide and Pd(OH)$_2$. Place the reaction on a Parr hydrogenator at 50 psi of H$_2$ and shake. Monitor the progress of the reaction by thin-layer chromatography. Upon completion of the reaction, remove the catalyst by suction filtration through celite. Remove solvent in vacuo to obtain the title compound.

Preparation 42

4-(3-Aminophenyl)-2-piperazinecarboxylic acid

In a manner similar to Preparation 17, react 4-(3-aminophenyl)-2-piperazinecarboxamide with potassium hydroxide to obtain the title compound.

Preparation 43

4-(3-Aminophenyl)-2-piperazinemethanol

In a manner similar to Preparation 18, react 4-(3-aminophenyl)-2-piperazinecarboxylic acid with borane dimethylsulfide to obtain the title compound.

Preparation 44

4-(2-Methyl-1H-imidazol-1-yl)benzenemethanol

In a manner similar to Preparation 18, react 4-(2-methyl-1H-imidazol-1-yl)benzoic acid with borane dimethylsulfide complex to obtain the title compound.

Preparation 45

1-(4-Chloromethylphenyl)-2-methyl-1H-imidazole

To 4-(2-methyl-1H-imidazole-1-yl)benzenemethanol add thionyl chloride. Monitor the progress of the reaction by thin-layer chromatography. Upon completion remove the excess thionyl chloride in vacuo. Partition the residue between 1N NaOH and CH$_2$Cl$_2$. Separate and dry the organic layer. Remove the solvent in vacuo to obtain the title compound.

Preparation 46

1-(3-Aminophenyl)-3-[[[4-(2-methyl-1H-imidazol-1-yl)phenyl]methoxy]methyl]piperazine In a manner similar to Preparation 19, react 4-(3-aminophenyl)-2-piperazinemethanol with 1-[4-(chloromethyl)phenyl]-2-methyl-1H-imidazole to obtain the title compound.

Preparation 47

N-(3,5-Dichlorophenyl)-2-[[(3,4-dimethoxyphenyl)methyl]amino]acetamide

In a manner similar to Preparation 12, react 2-chloro-N-(3,5-dichlorophenyl)acetamide with (3,4-dimethoxyphenyl)methanamine to obtain the title compound.

Preparation 48

N-(3,5-Dichlorophenyl)-N'-[(3,4-dimethoxyphenyl)methyl]-1,2-ethanediamine

In a manner similar to Preparation 2, react N-(3,5-dichlorophenyl)-2-[[(3,4-dimethoxyphenyl)methyl]amino]acetamide with lithium aluminum hydride to obtain the title compound.

Preparation 49

4-(3,5-Dichlorophenyl)-1-[(3,4-dimethoxyphenyl)methyl]-2-piperazinecarboxamide

In a manner similar to Preparation 1, react N-(3,5-dichlorophenyl)-N'-[(3,4-dimethoxyphenyl)methyl]-1,2-ethanediamine with 2,3-dibromopropanamide to obtain the title compound.

Preparation 50

4-(3,5-Dichlorophenyl)-1-[(3,4-dimethoxyphenyl)methyl]-2-piperazinecarboxylic acid In a manner similar to Preparation 17, react 4-(3,5-dichlorophenyl)-1-[(3,4-dimethoxyphenyl)methyl]-2-piperazinecarboxamide to obtain the title compound.

Preparation 51

4-(3,5-Dichlorophenyl)-1-[(3,4-dimethoxyphenyl)methyl]-2-piperazinemethanol

In a manner similar to Preparation 18, react 4-(3,5-dichlorophenyl)-1-[(3,4-dimethoxyphenyl)methyl]-2-piperazinecarboxylic acid with borane dimethylsulfide complex to obtain the title compound.

Preparation 52

4-(3,5-Dichlorophenyl)-1-[(3,4-dimethoxyphenyl)methyl]-2-[[(4-nitrophenyl)methoxy]methyl]piperazine In a manner similar to Preparation 19, react 4-(3,5-dichlorophenyl)-1-[(3,4-dimethoxyphenyl)methyl]-2-piperazinemethanol with sodium hydride and 1-

(chloromethyl)-4-nitrobenzene to give the title compound.

Preparation 53

N-[4-[[[4-(3,5-Dichlorophenyl)-1-[(3,4-dimethoxyphenyl)methyl]piperazin-2-yl]methoxy]methyl]phenyl]-methanesulfonamide In a manner similar to Preparation 27, react 4-(3,5-dichlorophenyl)-1-[(3,4-dimethoxyphenyl)methyl]-2-[[(4-nitrophenyl)methoxy]methyl]piperazine to obtain the title compound.

Preparation 54

N-(3,5-dimethoxyphenyl)-N'-(phenylmethyl)-1,2-ethanediamine

In a manner similar to Preparation 29, react 3,5-dimethoxybenzenamine with N-(2-chloroethyl)benzenemethanamine to obtain the title compound.

Preparation 55

4-(3,5-Dimethoxyphenyl)-1-(phenylmethyl)-2-piperazinecarboxamide

In a manner similar to Preparation 1, react N-(3,5-dimethoxyphenyl)-N'-(phenylmethyl)-1,2-ethanediamine with 2,3-dibromopropanamide to obtain the title compound.

Preparation 56

4-(3,5-Dimethoxyphenyl)-1-(phenylmethyl)-2-piperazinemethanamine

In a manner similar to Preparation 2, react 4-(3,5-dimethoxyphenyl)-1-(phenylmethyl)-2-piperazinecarboxamide with lithium aluminum hydride to obtain the title compound.

Preparation 57

N-[[4-(3,5-Dimethoxyphenyl)-1-(phenylmethyl)piperazin-2-yl]methyl]-4-[(ethylsulfonyl)amino]benzenesulfonamide In a manner similar to Preparation 3, react 4-(3,5-dimethoxyphenyl)-1-(phenylmethyl)-2-piperazinemethanamine with 4-[(ethylsulfonyl)amino]benzenesulfonyl chloride to obtain the title compound.

Preparation 58

N-(3-Bromo-5-methoxyphenyl)-2-chloroacetamide

In a manner similar to Preparation 3, react 3-bromo-5-methoxybenzeneamine with chloroacetyl chloride to obtain the title compound.

Preparation 59

N-(3-Bromo-5-methoxyphenyl)-2-[[(3,4-dimethoxyphenyl)methyl]amino]acetamide

In a manner similar to Preparation 12, react N-(3-bromo-5-methoxyphenyl)-2-chloroacetamide with 3,4-dimethoxybenzenemethanamine to obtain the title compound.

Preparation 60

N-(3-bromo-5-methoxyphenyl)-N'-[(3,4-dimethoxyphenyl)methyl]-1,2-ethanediamine

In a manner similar to Preparation 2, react N-(3-bromo-5-methoxyphenyl)-2-[[(3,4-dimethoxyphenyl)methyl]amino]acetamide with lithium aluminum hydride to obtain the title compound.

Preparation 61

4-(3-Bromo-5-methoxyphenyl)-1-[(3,4-dimethoxyphenyl)methyl]-2-piperazinecarboxamide In a manner similar to Preparation 1, react N-(3-bromo-5-methoxyphenyl)-N'-[(3,4-dimethoxyphenyl)methyl]-1,2-ethanediamine with 2,3-dibromopropanamide to obtain the title compound.

Preparation 62

4-(3-Bromo-5-methoxyphenyl)-1-[(3,4-dimethoxyphenyl)methyl]-2-piperazinemethanamine In a manner similar to Preparation 2, react 4-(3-bromo-5-methoxyphenyl)-1-[(3,4-dimethoxyphenyl)methyl]-2-piperazinecarboxamide with lithium aluminum hydride to obtain the title compound.

Preparation 63

4-(1H-Imidazol-1-yl)benzenesulfonyl chloride

To chlorosulfonic acid cooled to 0° C. in an ice bath is added portionwise 1-phenyl-1H-imidazole. Monitor the progress of the reaction by thin-layer chromatography. When the reaction is complete, quench the mixture on ice. Saturated aqueous $NaHCO_3$ is added until the solution is no longer acidic. Extract the mixture with $CH_2Cl_2$. Dry the organic layer over anhydrous $Na_2SO_4$ and remove the solvent in vacuo to obtain the title compound.

Preparation 64

N-[[4-(3-Bromo-5-methoxyphenyl)-1-[(3,4-dimethoxyphenyl)methyl]piperazin-2-yl]-methyl]-4-(1H-imidazol-1-yl)benzenesulfonamide In a manner similar to Preparation 3, react 4-(3-bromo-5-methoxyphenyl)-1-[(3,4-dimethoxyphenyl)methyl]-2-piperazinemethanamine with 4-(1H-imidazol-1-yl)benzenesulfonyl chloride to obtain the title compound.

Preparation 65

N-(2,6-Dichlorophenyl)-2-[[(3,4-dimethoxyphenyl)methyl]amino]acetamide

In a manner similar to Preparation 12, react 2-chloro-N-(2,6-dichlorophenyl)acetamide with 3,4-dimethoxybenzenemethanamine to obtain the title compound.

Preparation 66

N-(2,6-Dichlorophenyl)-N'-[(3,4-dimethoxyphenyl)methyl]-1,2-ethanediamine

In a manner similar to Preparation 2, react N-(2,6-dichlorophenyl)-2-[[(3,4-dimethoxyphenyl)methyl]amino]acetamide with lithium aluminum hydride to obtain the title compound.

Preparation 67

4-(2,6-Dichlorophenyl)-1-[(3,4-dimethoxyphenyl)methyl]-N-(2-propenyl)-2-piperazinecarboxamide In a manner similar to Preparation 23, react N-(2,6-dichlorophenyl)-N'-[(3,4-dimethoxyphenyl)methyl]-1,2-ethanediamine with 2,3-dibromo-N-(2-propenyl)-propanamide to obtain the title compound.

Preparation 68

4-(2,6-Dichlorophenyl)-1-[(3,4-dimethoxyphenyl)methyl]-N-(2-propenyl)-2-piperazinemethanamine In a manner similar to Preparation 2, react 4-(2,6-dichlorophenyl)-1-[(3,4-dimethoxyphenyl)methyl]-N-(2-propenyl)-2-piperazinecarboxamide with lithium aluminium hydride to obtain the title compound.

Preparation 69

N-[[4-(2,6-Dichlorophenyl)-1-[(3,4-dimethoxyphenyl)methyl]piperazin-2-yl]methyl]-4-[(methylsulfonyl)amino]-N-(2-propenyl)benzenesulfonamide In a manner similar to Preparation 3, react 4-(2,6-dichlorophenyl)-1-[(3,4-dimethoxyphenyl)methyl]-N-(2-propenyl)-2-piperazinemethanamine with 4-[(methylsulfonyl)amino]benzenesulfonyl chloride to obtain the title compound.

Preparation 70

N-(2-Methoxyethyl)-N-(4-nitrophenyl)-2-propenamide

In a manner similar to Preparation 3, react N-(2-methoxyethyl)-4-nitrobenzenamine with propenoyl chloride to obtain the title compound.

Preparation 71

2,3-Dibromo-N-(2-methoxyethyl)-N-(4-nitrophenyl)-propanamide

In a manner similar to Preparation 22, react N-(2-methoxyethyl)-N-(4-nitrophenyl)propenamide with bromine to obtain the title compound.

Preparation 72

N-(4-Ethoxyphenyl)-N'-(phenylmethyl)-1,2-ethanediamine

In a manner similar to Preparation 29, react 4-ethoxybenzenamine with N-(2-chloroethyl)benzenemethanamine to obtain the title compound.

Preparation 73

4-(4-Ethoxyphenyl)-N-(2-methoxyethyl)-N-(4-nitrophenyl)-1-(phenylmethyl)-2-piperazinecarboxamide In a manner similar to Preparation 23, react N-(4-ethoxyphenyl)-N'-(phenylmethyl)-1,2-ethanediamine with 2,3-dibromo-N-(2-methoxyethyl)-N-(4-nitrophenyl)propanamide to obtain the title compound.

Preparation 74

N-(4-Aminophenyl)-4-(4-ethoxyphenyl)-N-(2-methoxyethyl)-1-(phenylmethyl)-2-piperazinecarboxamide In a manner similar to Preparation 20, react 4-(4-ethoxyphenyl)-N-(2-methoxyethyl)-N-(4-nitrophenyl)-1-(phenylmethyl)-2-piperazinecarboxamide with tin II chloride to obtain the title compound.

Preparation 75

4-(4-Ethoxyphenyl)-N-(2-methoxyethyl)-N-[4-(2-methyl-1H-imidazol-1-yl)phenyl]-1-(phenylmethyl)-2-piperazinecarboxamide In a manner similar to Preparation 34, react N-(4-aminophenyl)-4-(4-ethoxyphenyl)-N-(2-methoxyethyl)-1-(phenylmethyl)-2-piperazinecarboxamide with glyceraldehyde, acetaldehyde and ammonium hydroxide to obtain the title compound.

Preparation 76

4-(4-Ethoxyphenyl)-N-(2-methoxyethyl)-N-[4-(2-methyl-1H-imidazol-1-yl)phenyl]-1-(phenylmethyl)-2-piperazinemethanamine In a manner similar to Preparation 2, react 4-(4-ethoxyphenyl)-N-(2-methoxyethyl)-N-[4-(2-methyl-1H-imidazol-1-yl)phenyl]-1-(phenylmethyl)-2-piperazinecarboxamide with lithium aluminum hydride to obtain the title compound.

Preparation 77

4-(3-Chlorophenyl)-1-[(3,4-dimethoxyphenyl)methyl]-N-(1-methylethyl)-2-piperazinecarboxamide In a manner similar to Preparation 23, react N-(3-chlorophenyl)-N'-[(3,4-dimethoxyphenyl)methyl]-1,2-ethanediamine with 2,3-dibromo-N-(1-methylethyl)-propanamide to obtain the title compound.

Preparation 78

4-(3-Chlorophenyl)-1-[(3,4-dimethoxyphenyl)methyl]-N-(1-methylethyl)-2-piperazinemethanamine In a manner similar to Preparation 2, react 4-(3-chlorophenyl)-1-[(3,4-dimethoxyphenyl)methyl]-N-(1-methylethyl)-2-piperazinecarboxamide with lithium aluminum hydride to obtain the title compound.

Preparation 79

N-[[4-(3-Chlorophenyl)-1-[(3,4-dimethoxyphenyl)methyl]piperazin-2-yl]methyl]-N-(1-methylethyl)-4-[(methylsulfonyl)amino]benzamide In a manner similar to Preparation 3, react 4-(3-chlorophenyl)-1-[(3,4-dimethoxyphenyl)methyl]-N-(1-methylethyl)-2-piperazinemethanamine with 4-[(methylsulfonyl)amino]benzoyl chloride to obtain the title compound.

Preparation 80

1-(3,4-Dichlorophenyl)-4-(1,1-dimethylethyl)-2-piperazinecarbonitrile

In a manner similar to preparation 1, react N-(3,4-dichlorophenyl)-N'-(1,1-dimethoxyethyl)-1,2-ethanediamine with 2,3-dibromopropanenitrile to obtain the title compound.

Preparation 81

1-(3,4-Dichlorophenyl)-4-(1,1-dimethylethyl)-2-piperazinemethanamine

In a manner similar to preparation 2, react 1-(3,4-dichlorophenyl)-4-(1,1-dimethylethyl)-2-piperazinecarbonitrile with lithium aluminum hydride to obtain the title compound.

Preparation 82

1-Methyl-4-phenyl-2-piperazinecarboxamide

In a manner similar to preparation 1, react N-methyl-N'-phenyl-1,2-ethanediamine with 2,3-dibromopropanamide to obtain the title compound.

Preparation 83

1-Methyl-4-phenyl-2-piperazinemethanamine

In a manner similar to preparation 2, react 1-methyl-4-phenyl-2-piperazinecarboxamide with lithium aluminum hydride to obtain the title compound.

Preparation 84

4-Butyl-1-(3,4-dimethoxyphenyl)-2-piperazinecarbonitrile

In a manner similar to preparation 1, react N-butyl-N'-(3,4-dimethoxyphenyl)-1,2-ethanediamine with 2-chloro-2-propenenitrile to obtain the title compound.

Preparation 85

4-Butyl-1-(3,4-dimethoxyphenyl)-2-piperazinemethanamine

In a manner similar to preparation 2, react 4-butyl-1-(3,4-dimethoxyphenyl)-2-piperazinecarbonitrile with lithium aluminum hydride to obtain the title compound.

Preparation 86

4-(3,4-Dichlorophenyl)-1-ethyl-N-(4-nitrophenyl)-2-piperazinecarboxamide

In a manner similar to preparation 23, react N-(3,4-dichlorophenyl)-N'-ethyl-1,2-ethanediamine with 2,3-dibromo-N-(4-nitrophenyl)propanamide to obtain the title compound.

Preparation 87

N-(4-Aminophenyl)-4-(3,4-dichlorophenyl)-1-ethyl-2-piperazinecarboxamide

In a manner similar to preparation 20, react 4-(3,4-dichlorophenyl)-1-ethyl-N-(4-nitrophenyl)-2-piperazinecarboxamide with tin II chloride to obtain the title compound.

Preparation 88

4-(3,4-Dichlorophenyl)-1-ethyl-N-[4-(1H-imidazol-1-yl)phenyl]-2-piperazinecarboxamide In a manner similar to preparation 34, react N-(4-aminophenyl)-4-(3,4-dichlorophenyl)-1-ethyl-2-piperazinecarboxamide, ammonium hydroxide, aqueous formaldehyde, and glyoxal to obtain the title compound.

EXAMPLES

EXAMPLE 1

4-[(Methylsulfonyl)amino]-N-[(4-phenylpiperazin-2-yl)methyl]benzamide hydrochloride To methanol (400 mL) add 4-[(methylsulfonyl)amino]-N-[[4-phenyl-1-(phenylmethyl)piperazin-2-yl]methyl]benzamide hydrochloride (40 g, 77 mmol) and Pd(OH)$_2$ (2.0 g). When the addition is complete, place the reaction mixture on a Parr hydrogenator at 50 p.s.i. of H$_2$ and shake. Monitor the progress of the reaction by thin-layer chromatography. Upon completion of the reaction, remove the catalyst by suction filtration through celite. Wash the pad with methanol. Remove the solvent in vacuo to obtain a residue. Recrystallize from methanol to provide the title compound.

NMR (DMSO-d$_6$): $\delta = 2.98(dd,1)$, 3.07(s,3), 3.1(m,1), 3.3–3.9(m,7), 6.87(t,1), 7.00(d,2), 7.3(m,4), 7.97(d,2), 8.88(t,1), 9.54(br,2) and 10.2(br,1)ppm.

EXAMPLE 2

N-[4-[[[(4-Phenylpiperazin-2-yl)methyl]amino]methyl]phenyl]methanesulfonamide, sulfuric acid salt To 4-[(methylsulfonyl)amino]-N-[(4-phenylpiperazin-2-yl)methyl]benzamide (3.2 g, 8.2 mmol) in tetrahydrofuran (10 mL) add borane dimethylsulfide (2.5 mL, 25 mmol). Stir and heat the reaction under nitrogen at reflux. Monitor the progress of the reaction by thin-layer chromatography. Upon completion of the reaction, add methanolic hydrochloric acid dropwise. Continue to reflux the reaction for 2 h. Remove the solvent in vacuo. Dissolve the material in methanol/H$_2$O and add the ion exchange resin AG 1-X8 until the pH is 8. The resin is removed by filtration and remove the solvent in vacuo. Dissolve the residue in methanol and add concentrated H$_2$SO$_4$ (0.23 mL, 4.3 mmol) to give the title compound which precipitates from the solution.

NMR (DMSO-d$_6$): $\delta = 2.65(t,1)$, 2.7–2.9(m,3), 2.98(s,3), 3.00(m,1), 3.26(m,2), 3.6(d,1), 3.7(d,1), 3.81(d,1), 3.84(d,1), 4.0(br s,2), 6.84(t,1), 6.97(t,2), 7.19(d,2), 7.26(d,2), 7.39(d,2) and 9.8(br,1)ppm.

EXAMPLE 3

4-[(Methylsulfonyl)amino]-N-[(1-phenylpiperazin-2-yl)methyl]benzamide

To methanol (500 mL) under nitrogen atmosphere add 4-[(methylsulfonyl)amino]-N-[1-phenyl-4-(phenylmethyl)piperazin-2-yl]methyl]benzamide (10.4 g, 21.7 mmol), ammonium formate (27.4 g, 4.34 mmol) and Pd/C (1.0 g) and reflux. Monitor the progress of the reaction by thin-layer chromatography. Upon completion of the reaction, remove the catalyst by suction filtration through celite. Wash the pad with methanol. Remove the solvent in vacuo. Add water to the residue and adjust the pH to 8.5 with dilute sodium hydroxide solution. Extract the mixture with methylene chloride/2-propanol (9/1). Repeat this extraction two times. Concentrate the organic layers to give a white solid. Recrystallize from acetonitrile/methanol to provide the title compound.

NMR (DMSO-d$_6$): $\delta = 2.75(m,2)$, 3.00(m,3), 3.07(s,3), 3.30(m,2), 3.68(m,1), 3.95(m,1), 6.69(t,1), 7.00(d,2), 7.21(m,4), 7.45(d,2) and 8.46(t,1)ppm.

EXAMPLE 4

4-(1H-Imidazol-1-yl)-N-[(4-phenylpiperazin-2-yl)methyl]benzamide trihydrochloride In a manner similar to Example 1, react 4-(1H-imidazol-1-yl)-N-[[4-phenyl-1-(phenylmethyl)piperazin-2-yl]methyl]benzamide trihydrochloride (12.3 g, 22 mmol) with H$_2$ over Pd(OH)$_2$ (1.5 g) catalyst to give the title compound.

NMR (DMSO-d$_6$): $\delta = 3.2(m,3)$, 3.44(m,1), 3.56–3.94(m,5), 4.7–6.2(br, 2+H$_2$O), 6.90(t,1), 7.06(d,2), 7.20(m,2), 8.02(m,3), 8.28(d,2), 8.46(s,1), 9.31(t,1) and 9.84–10.14(m,3)ppm.

EXAMPLE 5

N-[[4-(3-Methoxyphenyl)piperazin-2-yl]methyl]-4-[(methylsulfonyl)amino]benzamide dihydrochloride In a manner similar to Example 1, react 4-[(methylsulfonyl)amino]-N-[[4-(3-methoxyphenyl)-1-(phenylmethyl)piperazin-2-yl]methyl]benzamide dihydrochloride (2.3 g, 4 mmol) with H$_2$ over Pd(OH)$_2$ (0.3 g) catalyst to give the title compound.

NMR (DMSO-d$_6$): $\delta = 3.00-3.30(m,3)$, 3.08(s,3), 3.40(d,1), 3.50–3.90(m,4), 3.73(s,3), 6.49(dd,1), 6.54–6.66(m,2), 7.19(t,1), 7.30(d,2), 8.00(d,2), 8.25(br s,2), 8.95(t,1), 9.60–9.90(m,2), 10.27(s,1)ppm.

EXAMPLE 6

N-[[4-(2-Methoxyphenyl)piperazin-2-yl]methyl]-4-[(methylsulfonyl)amino]benzamide hydrochloride In a manner similar to Example 1, react N-[[4-(2-methoxyphenyl)-1-(phenylmethyl)piperazin-2-yl]methyl]-4-[(methylsulfonyl)amino]benzamide hydrochloride (8.7 g, 16 mmol) with $H_2$ over Pd(OH)$_2$ (0.2 g) catalyst to give the title compound.

NMR (DMSO-d$_6$): $\delta$=2.9(dd,1), 3.07(s,3), 3.0–3.2(m,4), 3.3–3.7(m,5), 3.74(s,3), 3.8(m,1), 6.8–7.1(m,4), 7.29(d,2), 7.95(d,2), 8.85(t,1), 9.6(br,2) and 10.2(br,1)ppm.

EXAMPLE 7

N-[4-[(4-Phenylpiperazin-2-yl)methoxy]phenyl]methanesulfonamide hydrochloride

In a manner similar to Example 1, hydrogenolyze N-[4-[[4-phenyl-1-(phenyl-methyl)piperazin-2-yl]methoxy]phenyl]methanesulfonamide hydrochloride (7.4 g, 15 mmol) to give the title compound.

NMR (DMSO-d$_6$): $\delta$2.90(s,3), 3.1(m,3), 3.4(m,1), 3.75(m,2), 3.91(m,1), 4.28(m,2), 6.86(t,1), 7.03(m,4), 7.22(m,4), 9.51(s,1) and 9.65(br s,2)ppm.

EXAMPLE 8

N-[4-[[(4-Phenylpiperazin-2-yl)methyl]amino]phenyl]methanesulfonamide

In a manner similar to Example 1, react N-[4-[[[4-phenyl-1-(phenylmethyl)piperazin-2-yl]methyl]amino]phenyl]methanesulfonamide hydrochloride (2.05 g, 4.22 mmol) with $H_2$ over 10% palladium on activated carbon (0.19 g). Remove the catalyst by filtration and evaporate the solvent. Dissolve the residue in methanol and adjust the pH to 8 with 4M aqueous NaOH. Remove the solvent in vacuo. Triturate the residue with methylene chloride. Remove the solid by filtration. Recrystallize the residue from methylene chloride to obtain the title compound.

NMR (DMSO-d$_6$): $\delta$=2.61(dd,1), 2.82(td,1), 2.93(s,3), 3.04(td,1), 3.11–3.35(m,4), 3.56(m,2), 4.18(br s,1), 6.08(br,1), 6.65(d,2), 6.91(t,1), 6.97(d,2), 7.12(d,2) and 7.30(m,2)ppm.

EXAMPLE 9

N-[4-[[(1-Phenylpiperazin-2-yl)methyl]amino]phenyl]methanesulfonamide

In a manner similar to Example 1, react N-[4-[[[1-phenyl-4-(phenylmethyl)piperazin-2-yl]methyl]amino]phenyl]methanesulfonamide, hydrochloride (2.92 g, 6.0 mmol) with $H_2$ over 10% palladium on activated charcoal (0.29 g). Chromatograph the residue on silica with CH$_3$CN/NH$_4$OH (99/1) to obtain the title compound.

NMR (CDCl$_3$): $\delta$=2.89(s,3), 2.96(m,1), 3.05–3.32(m,6), 3.46(m,1), 3.90(m,1), 4.12(br,1), 6.44(d,2), 6.87(t,1), 6.93(d,2), 7.02(d,2) and 7.26(m,2)ppm.

EXAMPLE 10

N-[[4-[3-(1H-Imidazol-1-yl)phenyl]piperazin-2-yl]methyl]-4-[(methylsulfonyl)amino]benzamide, hydrochloride In a manner similar to Example 1, react N-[[4-[3-(1H-imidazol-1-yl)phenyl-]-1-(phenylmethyl)piperazin-2-yl]methyl]-4-[(methylsulfonyl)amino]benzamide hydrochloride (2.5 g, 4.4 mmol) with $H_2$ over Pd on carbon (1.2 g) to obtain the title compound.

NMR (DMSO-d$_6$): $\delta$=3.01(m,1), 3.07(s,3), 3.15(m,2), 3.52(m,2), 3.65(m,2), 3.86(m,1), 3.98(d,1), 6.99(dd,1), 7.11(dd,1), 7.12(s,1), 7.25(d,2), 7.29(s,1), 7.39(t,1), 7.77(s,1), 7.94(d,2), 8.30(s,1), 8.80(t,1), 9.4(br,2) and 10.2(br s,1)ppm.

EXAMPLE 11

N-[[4-(3-Chlorophenyl)piperazin-2-yl]methyl]-4-[(methylsulfonyl)amino]benzamide

To a 5% solution of concentrated sulfuric acid in anhydrous trifluoroacetic acid (12 mL) under nitrogen atmosphere, add 4-[(methylsulfonyl)amino]-N-[[4-(3-chloropohenyl)-1-(3,4-dimethoxyphenylmethyl)piperazin-2-yl]methyl]benzamide (2.6 g, 5 mmol) and methoxybenzene (1.1 g, 10 mmol) and heat at 60° C. Monitor the progress of the reaction by thin-layer chromatography. Upon completion of the reaction add water (5 mL), 1N NaOH (10 mL) and saturated NaHCO$_3$ (10 mL) and extract this mixture with methylene chloride. Concentrate the organic layer. Flash chromatograph the oil on silica (100 g) with acetonitrile first, then a mixture of acetonitrile/methanol (85/15). Combine and concentrate the fractions containing product. Dissolve the oil in methanol and add a solution of hydrogen chloride in methanol. Remove the solvent in vacuo and recrystallize from acetonitrile/methanol to provide the title compound.

NMR (DMSO-d$_6$): $\delta$=2.95–3.22(m,2), 3.07(s,3), 3.32–3.55(m,2), 3.58–3.92(m,5), 6.90(d,1), 7.07(d,1), 7.24(s,1), 7.28(m,3), 7.96(d,2), 8.87(t,1), 9.38–9.68(m,2), and 10.22(s,1)ppm.

EXAMPLE 12

4-[(Methyl)(methylsulfonyl)amino]-N-[(4-phenylpiperazin-2-yl)methyl]benzamide, hydrochloride In a manner similar to Example 1, react 4-[(methyl)-(methylsulfonyl)amino]-N-[4-phenyl-1-(phenylmethyl)-piperazin-2-yl]methyl]benzamide, dihydrochloride (8.0 g, 14.2 mmol) with $H_2$ over 10% palladium on carbon (0.7 g) to obtain the title compound.

NMR (DMSO-d$_6$): $\delta$=2.90(m,1), 2.99(s,3), 2.98–3.20(m,2), 3.28(s,3), 3.4(m,2), 3.55–3.75(m,3), 3.80(m,1), 6.84(t,1), 7.01(d,2), 7.26(t,2), 7.53(d,2), 7.95(d,2), 8.82(t,1) and 9.0(br,2)ppm.

EXAMPLE 13

1-[3-(1H-Imidazol-1-yl)phenyl[-3-[[[4-(2-methyl-1H-imidazol-1-yl)phenyl]methoxy]methyl]piperazine In a manner similar to Preparation 34, react 1-(3-aminophenyl)-3-[[[4-(2-methyl-1H-imidazol-1-yl)phenyl]methoxy]methyl]piperazine with glyoxal, formaldehyde, and ammonium acetate to obtain the title compound.

EXAMPLE 14

N-[4-[[[4-(3,5-Dichlorophenyl)piperazin-2-yl]methoxy]methyl]phenyl]methanesulfonamide In a manner similar to Example 11, react N-[4-[[[4-(3,5-dichlorophenyl)-1-[(3,4-dimethoxyphenyl)methyl]-piperazin-2-yl]methoxy]methyl]phenyl]methanesulfonamide with methoxybenzene and a 5% solution of concentrated H$_2$SO$_4$ in trifluoroacetic acid to obtain the title compound.

EXAMPLE 15

N-[[4-(3,5-Dimethoxyphenyl)piperazin-2-yl]methyl]-4-[(ethylsulfonyl)amino]benzenesulfonamide In a manner similar to Example 1, hydrogenolyze N-[[4-(3,5-dimethoxyphenyl)-1-(phenylmethyl)piperazin-2-yl]methyl]-4-[(ethylsulfonyl)amino]benzenesulfonamide over Pd(OH)$_2$ to obtain the title compound.

EXAMPLE 16

N-[[4-(3-Bromo-5-methoxyphenyl)piperazin-2-yl]methyl]-4-(1H-imidazol-1-yl)benzenesulfonamide In a manner similar to Example 11, react N-[[4-(3-bromo-5-methoxyphenyl)-1-[(3,4-dimethoxyphenyl)methyl]piperazin-2-yl]methyl]-4-(1H-imidazol-1-yl)benzenesulfonamide with methoxybenzene and a 5% solution of concentrated H$_2$SO$_4$ in trifluoroacetic acid to obtain the title compound.

EXAMPLE 17

N-[[4-(2,6-Dichlorophenyl)piperazin-2-yl]methyl]-4-[(methylsulfonyl)amino]-N-(2-propenyl)benzenesulfonamide In a manner similar to Example 11, react N-[[4-(2,6-dichlorophenyl)-1-[(3,4-dimethoxyphenyl)methyl]piperazin-2-yl]methyl]-4-[(methylsulfonyl)amino]-N-(2-propenyl)benzenesulfonamide with methoxybenzene and a 5% solution of concentrated H$_2$SO$_4$ in trifluoroacetic acid to obtain the title compound.

EXAMPLE 18

4-(4-Ethoxyphenyl)-N-(2-methoxyethyl)-N-[4-(2-methyl-1H-imidazol-1-yl)phenyl]-2-piperazinemethanamine In a manner similar to Example 1, hydrogenolyze 4-(4-ethoxyphenyl)-N-(2-methoxyethyl)-N-[4-(2-methyl-1H-imidazol-1-yl)phenyl]-1-(phenylmethyl)-2-piperazinemethanamine over Pd(OH)$_2$ to obtain the title compound.

EXAMPLE 19

N-[[4-(3-Chlorophenyl)piperazin-2-yl]methyl]-N-(1-methylethyl)-4-[(methylsulfonyl)amino]benzamide In a manner similar to Example 11, react N-[[4-(3-chlorophenyl)-1-[(3,4-dimethoxyphenyl)methyl]piperazin-2-yl]methyl]-N-(1-methylethyl)-4-[(methylsulfonyl)amino]benzamide with methoxybenzene and a 5% solution of concentrated H$_2$SO$_4$ in trifluoroacetic acid to obtain the title compound.

EXAMPLE 20

N-[[1-(3,4-Dichlorophenyl)-4-(1,1-dimethylethyl)piperazin-2-yl]methyl]-4-(1H-imidazol-1-yl)benzamide In a manner similar to preparation 7, react 4-(1H-imidazol-1-yl)benzoic acid, 1,1-carbonyldiimidazole and 1-(3,4-dichlorophenyl)-4-(1,1-dimethylethyl)-2-piperazinemethanamine to obtain the title compound.

EXAMPLE 21

N-[(1-Methyl-4-phenylpiperazin-2-yl)methyl]-4-[(methylsulfonyl)amino]benzamide

In a manner similar to preparation 3, react 1-methyl-4-phenyl-2-piperazinemethanamine with 4-[(methylsulfonyl)amino]benzoyl chloride to obtain the title compound.

EXAMPLE 22

N-[[4-Butyl-1-(3,4-dimethoxyphenyl)piperazin-2-yl]methyl]-4-[(methylsulfonyl)amino]benzenesulfonamide In a manner similar to preparation 3, react 4-butyl-1-(3,4-dimethoxyphenyl)-2-piperazinemethanamine with 4-[(methylsulfonyl)amino]sulfonyl chloride to obtain the title compound.

EXAMPLE 23

4-(3,4-Dichlorophenyl)-1-ethyl-N-[4-(1H-imidazol-1-yl)phenyl]-2-piperazinemethanamine In a manner similar to preparation 2, react 4-(3,4-dichlorophenyl)-1-ethyl-N-[4-(1H-imidazol-1-yl)phenyl]-2-piperazinecarboxamide with lithium aluminum hydride to obtain the title compound.

We claim:

1. A compound of the following Formula I:

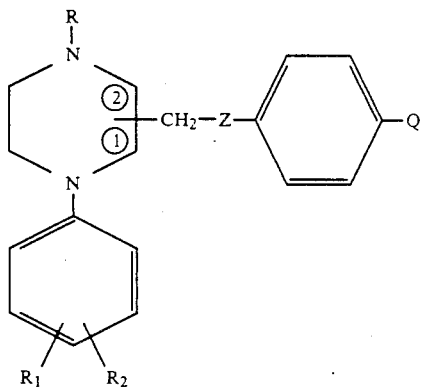

wherein
R is hydrogen, lower alkyl or benzyl;
R$_1$ and R$_2$ are the same or independently hydrogen, lower alkyl, lower alkoxy or halogen;
Z is

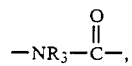

—NR$_3$—CH$_2$—, —O—CH$_2$—, —NR$_3$—, —O— or —NR$_3$SO$_2$—;
Q is (C$_1$-C$_4$)—SO$_2$—NR$_4$— or

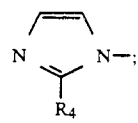

R$_3$ is hydrogen, lower alkyl, allyl, loweralkoxyloweralkyl;
R$_4$ is hydrogen or methyl;
and the pharmaceutically acceptable slats thereof;
provided that,
when R$_4$ is methyl then

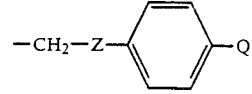

must be in the ② position of Formula I.

2. A compound of claim 1 where R and R$_4$ are hydrogen and

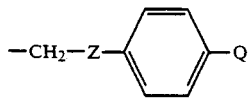

is in the ② position of Formula I.

3. A compound of claim 1 where R and R$_4$ are hydrogen and

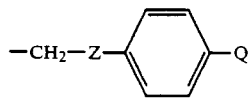

is in the ① position of Formula I.

4. A compound of claim 1 where R is not hydrogen and R$_4$ is hydrogen.

5. A compound of claim 1 where R is hydrogen and R$_4$ is methyl and

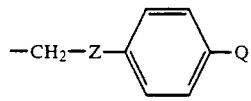

is in the ② position of Formula I.

6. A compound of claim 2 which is N-[4-[[[(4-phenylpiperazin-2-yl)methyl]amino]methyl]phenyl]methanesulfonamide.

7. A compound of claim 2 which is N-[4-[[(4-phenylpiperazin-2-yl)methyl]amino]phenyl]methanesulfonamide.

8. A compound of claim 2 which is 4-[(methylsulfonyl)amino]-N-[(4-phenylpiperazin-2-yl)methyl]benzamide.

9. A compound of claim 2 which is 4-(1H-imidazol-1-yl)-N-[(4-phenylpiperazin-2-yl)methyl]benzamide.

10. A compound of claim 2 which is N-[[4-(3-methoxyphenyl)piperazin-2-yl]methyl]-4-[(methylsulfonyl)amino]benzamide.

11. A compound of claim 2 which is N-[[4-(2-methoxyphenyl)piperazin-2-yl]methyl]-4-[(methylsulfonyl)amino]benzamide.

12. A compound of claim 2 which is N-[4-[(4-phenylpiperazin-2-yl)methoxy]phenyl]methanesulfoxamide.

13. A compound of claim 2 which is N-[[4-(3-chlorophenyl)piperazin-2-yl]methyl]-4-[(methylsulfonyl)amino]benzamide.

14. A compound of claim 3 which is 4-[(methylsulfonyl)amino]-N-[(1-phenylpiperazin-2-yl)methyl]benzamide.

15. A compound of claim 3 which is N-[4-[[(1-phenylpiperazin-2-yl)methyl]amino]phenyl]methanesulfonamide.

16. A compound of claim 5 which is 4-[(methyl)(methylsulfonyl)amino]-N-[(4-phenylpiperazin-2-yl)methyl]benzamide.

17. A pharmaceutical composition comprising at least one compound according to claim 1, together with one or more non-toxic pharmaceutically acceptable carriers.

* * * * *